United States Patent [19]

Butler

[11] 4,062,750
[45] Dec. 13, 1977

[54] THIN FILM ELECTROCHEMICAL ELECTRODE AND CELL

[76] Inventor: James Francis Butler, 41 Dundonald St., Suite 902, Toronto, Ontario, Canada, M4Y 1K6

[21] Appl. No.: 534,049

[22] Filed: Dec. 18, 1974

[51] Int. Cl.² ............... G01N 27/30; G01N 27/50
[52] U.S. Cl. ................... 204/195 P; 204/15; 204/279; 204/290 R; 204/290 F
[58] Field of Search ............ 204/195 P, 195 B, 15, 204/279, 280, 195, 290 R, 290 F

[56] References Cited

U.S. PATENT DOCUMENTS

| | | | |
|---|---|---|---|
| 3,162,589 | 12/1964 | Pensak | 204/15 X |
| 3,188,251 | 6/1965 | Straight et al. | 204/15 UX |
| 3,313,721 | 4/1967 | Teel | 204/290 F X |
| 3,449,221 | 6/1969 | Thomas | 204/15 |
| 3,462,349 | 8/1969 | Georenyi | 204/15 |
| 3,926,747 | 12/1975 | Newby et al. | 204/15 |

Primary Examiner—G. L. Kaplan
Attorney, Agent, or Firm—Rogers, Bereskin & Parr

[57] ABSTRACT

A thin film polarographic oxygen sensor, in which a number of thin film microcathodes are deposited in holes in a thin film layer of silicon dioxide formed on a silicon substrate. A single thin film anode layer is deposited on the insulating layer and is insulated thereby from the cathodes. Preferably the microcathodes and the anode are located in a well in the thin film insulating layer, the well being filled flush to its surface with electrolyte, and having a thin film polymer filter membrane deposited thereover. Contacts to the anode and cathodes may be punched through a thin film insulating layer on the back of the wafer, the cathode contact being thereby connected to the substrate, and the anode contact being insulated from the substrate by an encircling thin film layer of silicon dioxide and extending through to the anode metallization layer. With appropriate choice of electrode, electrolyte and membrane materials, the cell may also be used as a pH sensor, a $CO_2$ sensor, a specific ion sensor, or to detect or sense other substances in solution. Single electrode units may also be formed by depositing thin film electrode materials on appropriate substrates.

12 Claims, 29 Drawing Figures

THIN FILM ELECTROCHEMICAL ELECTRODE AND CELL

This invention relates to an electro-chemical cell and electrode and to a method for making the same. The invention will be described primarily with reference to an oxygen sensor, but many further applications of the invention exist, as will be explained.

It is well known to measure the oxygen content of a fluid (often expressed in terms of the oxygen partial pressure, $Po_2$, either of the gas under measurement or of an oxygen-containing gas mixture in equilibrium with the liquid under measurement) by a polarographic method. Such a method involves the setting up of an electro-chemical cell having an electrode assembly comprising an indicator-electrode (or oxygen cathode) of a noble metal and a reference - electrode (or anode). A current flows in the cell as a result of chemical processes occuring at the electrodes and as a result either of a polarising voltage externally applied between the electrodes or of a favourable reference-electrode electrode potential (the reference-electrode is required to provide electrical continuity to the fluid under measurement and advantageously has a constant electrode potential regardless of changes occuring in the fluid). At sufficiently high polarising voltage levels the current flowing through the polarographic cell is proportional to the number of oxygen molecules arriving at the oxygen cathode per unit time and since this number is governed by the oxygen partial pressure, the current is proportional to $PO_2$. If desired, the polarographic cell may be protected by a surrounding membrane which facilitates electrochemical isolation of the cell electrolyte from the fluid under measurement but which allows diffusion therethrough of oxygen contained in the fluid under measurement.

Previous oxygen sensors have had numerous disadvantages. They have, so far as the applicant is aware, usually been large, and have been made from a number of separate pieces which have had to be carefully assembled together. They have been expensive to manufacture and have required frequent servicing. In addition, they have commonly given readings which are not reproducible. Since for example when reading patient blood oxygen levels, accurate readings may be critical to the health or life of the patient, prior art oxygen sensors have all too commonly proven unsatisfactory.

Accordingly, it is an object of the present invention in one of its aspects to provide an improved oxygen sensor and a method for making the same. This aspect of the invention is accomplished by forming the oxygen sensor as a single integrated unit, employing thin film deposition techniques.

It is more generally an object of the invention to provide a method for forming electro-chemical cells by means of thin film deposition techniques, and to provide thin film electro-chemical cells. Such cells may be used, not only as oxygen sensors, but also in many other applications. Such applications may include, for example, the sensing or detection of gases other than oxygen, the detection of pH, readings of specific ion ratios, generation of electricity (when used in a fuel cell mode), and the detection of other chemical or physical parameters. The invention also provides a method of forming single electrodes for use in electrochemical cells, and thin film electrodes so formed.

A further object of the invention, in one of its aspects, is to provide an improved method for forming a thin film electro-chemical cell or electrode, in which connections are made through the back of the cell or electrode. Preferably in addition the electrode substance(s) of the cell or electrode is(are) located in a well formed in the front surface of the cell, facilitating deposition of an electrolyte and protective membrane where required and enabling the wafer on which the units are formed to be broken apart readily to release the units.

Further objects and advantages of the invention will appear from the following description, taken together with the accompanying drawings, in which.

Figure 3:
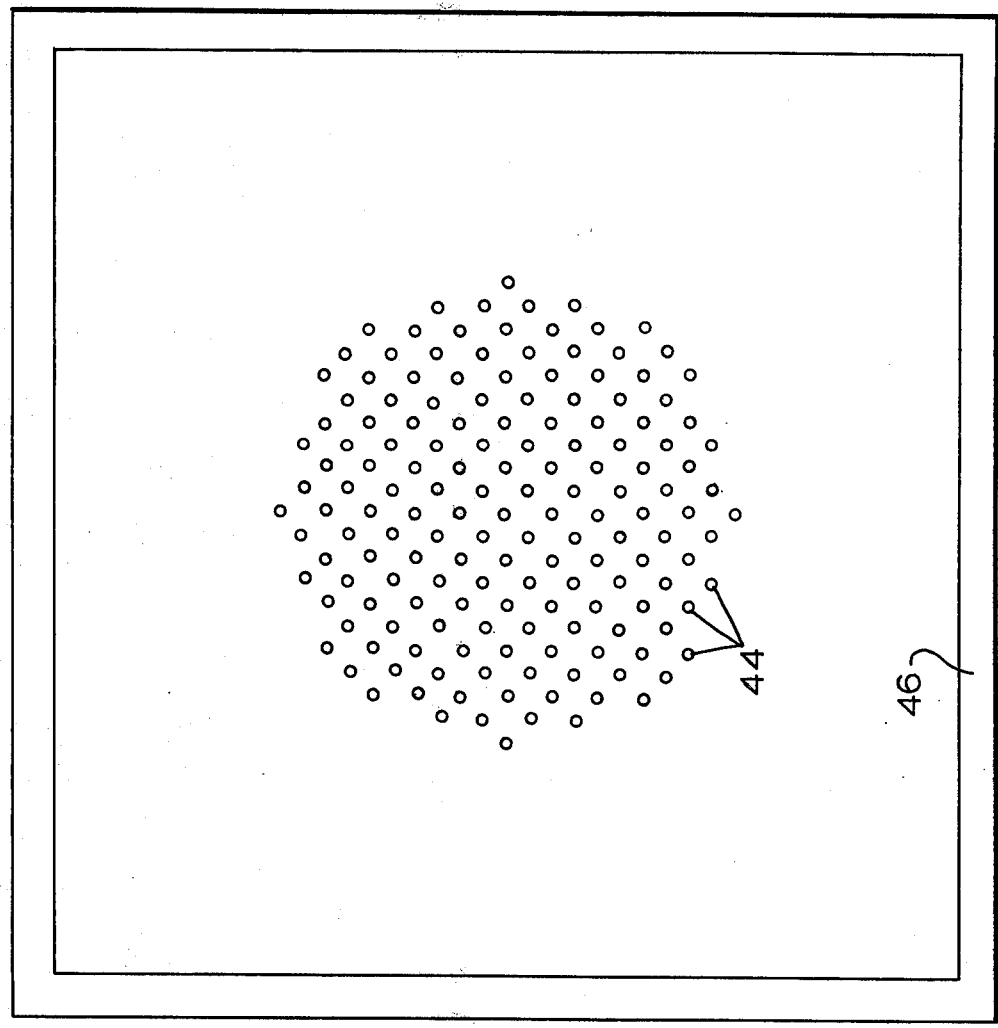
FIG. 3 shows a cathode pattern mask used in fabrication of the electrode assembly of FIG. 1.

An illustrative embodiment of the invention will now be described with reference to FIGS. 1 to 8 inclusive. This embodiment is exemplary only and shall not be taken as limiting the scope of the appended claims.

Reference is first made to FIGS. 1 to 4, which show diagrammatically a prototype polarographic oxygen sensor in a simple configuration for testing fluid samples. The sensor, which is generally indicated at 2, comprises an electrode assembly 10 (shown in detail in FIG.

2) which is secured by a conducting epoxy resin to a copper cylinder 11. The cylinder 11 is positioned behind a Teflon-on-Cellophane membrane 12. ("Teflon" is a trade mark for a polytetrafluoroethylene; "Cellophane" is a trade mark for a cellulose film.)

The copper cylinder 11 is soldered onto a TO-18 transistor header 13 (which is about ¼ inch in diameter) which is sealed, in a brass cylinder 14 by an insulating epoxy resin 15. The brass cylinder 14 is mounted on a plastic cylinder 16. The TO-18 transistor header 13 comprises a metal body 17 and four leads encased at one end in a glass insulator 18. Three of the leads 19 (only one is shown) terminate in pins on the top of the metal body 17 and the fourth lead 20 is connected to the metal body 17. The pins of the header 13 are connected by a silver metallization 21 to the anode (to be described) of the electrode assembly 10, and the leads 19 connected to the pins therefore enable external connection to the anode. The cathodes (to be described) of the electrode assembly 10 are electrically connected to the fourth lead 20 via the conducting epoxy resin, the copper cylinder 11 and metal body 17.

The membrane 12 is fixed in position over the electrode assembly 10 by a rubber O-ring 22. A buffered electrolyte 23 is contained between the membrane 12 and the main body of the sensor. A ring 24 of a suitable material (a dense inert plastic polymer) is sealed to the top end surface of the brass cylinder 14 to prevent any electro-chemical reaction between the electrodes and brass surfaces wet by the electrolyte.

Figure 2:
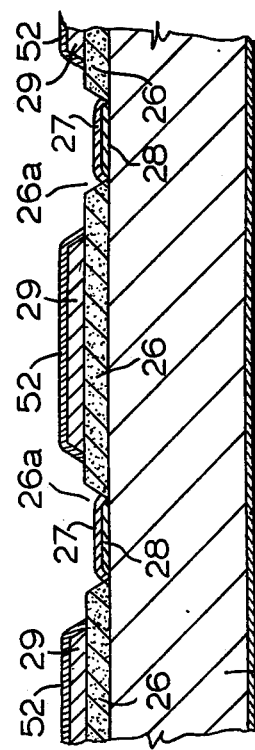
FIG. 2 is a cross-section through part of an electrode assembly of the sensor of FIG. 1.

The electrode assembly 10 is constructed using integrated circuit thin film techniques which allow precise dimensional control over the electrode layout. An enlarged cross-section of part of the electrode assembly is shown in FIG. 2. The electrode assembly comprises a silicon dioxide layer 26 formed on a highly conducting silicon substrate 25, for example a p-type silicon substrate. Gold cathodes 27 are formed on a chromium layer 28 formed on the silicon substrate 25 in circular areas where the silicon dioxide layer 26 has been selectively etched away. The intermediate chromium layer is used to obtain a good adhesion between the gold cathodes 27 and the main body of the electrode assembly. A single silver anode 29 is formed on the top face of the silicon dioxide and is arranged to be well insulated from the gold cathodes 27. An aluminum layer 37 on the back side of the silicon substrate 25 ensures a good ohmic contact with the copper cylinder 11.

In this particular embodiment of the electrode assembly, there are 161 cathodes, each $7 \pm 0.3\mu$ in diameter and spaced $60\mu$ from each other in a roughly circular array. (The form of this array can be seen in FIGS. 3 and 4.) The silver anode 29 has a side of length 0.85 mm, this dimension constituting the minimum size of a finished sensor which utilizes an electrode assembly of this size. The silver anode 29 is isolated from the gold cathodes 27 by the silicon dioxide layer 26 and by an exposed ring of the silicon dioxide of $25 \pm 1\mu$ outside diameter. Approximate theoretical treatment indicates that the anode area must be at least 30 times the cathode area to prevent polarization effects occuring. The described electrode assembly has an anode to cathode area ratio of 50:1 which thus ensures that the Ag/AgCl anode is non-polarized and that the diffusion zone of each cathode does not intrude on its neighbours even at high fluid flow rates.

The sensitivity of such a sensor is approximately 161 times that of other sensors of the same dimensions. With a suitable choice of membrane, the flow dependence and time constant are substantially the same as for an oxygen electrode with a $7\mu$ cathode.

The described electrode assembly can be advantageously used for polarographic oxygen sensing in gases and fluids at any rate of flow.

The fabrication process of the electrode assembly 10 will not be described.

Precise dimensional control of the electrode structure of the electrode assembly 10 is obtained through the use of an acid-resistant light-sensitive lacquer (photoresist). This material permits high-resolution photoengraving and thin film forming operations, to be perfomred reliably. Photoresist techniques, enable dimensions to be controlled to a precision approaching $1\mu$.

The electrode assembly fabrication process basically consisted of four parts:

1. substrate preparation (using the mask 40 shown in FIG. 3);
2. metallization;
3. thin film silver etching (using the mask 42 shown in FIG. 4); and
4. finishing.

A detailed step-by-step analysis of one process sequence for fabrication of the electrode assembly 10 is given in Table 1.

TABLE 1

| STEP NUMBER | PROCESS STEP | METHOD OR PROCEDURE | TIME | OTHER PROCESS DETAILS. Unless otherwise state the temperature is average room value of 25° C |
|---|---|---|---|---|
| 1 | Oxidize the Si Wafer 25 (forming the SiO₂ layer 26) | Thermal oxidation in moist nitrogen | 40 minutes | — temperature: 1050° C SiO₂ thickness: 5000 A |
| 2 | Cool and dry the wafer 25 | In a clean, dry atmosphere | | |
| 3 | Coat wafer 25 | Spin coat at 5000 rpm with KODAK Micro Resist 747 (trade mark) | 30 seconds | — room temperature<br>— under laminar flow clean air<br>— 0.5μ filtration just before application |
| 4 | Prebake the resist coat | In a convection oven | 20 minutes | — temperature: 90° C |
| 5 | Expose the resist coat | With a Quartz Iodine lamp | As Required | — cathode pattern mask (FIG. 3)<br>— nitrogen curtain for 2 minutes before producing |

TABLE 1-continued

| STEP NUMBER | PROCESS STEP | METHOD OR PROCEDURE | TIME | OTHER PROCESS DETAILS. Unless otherwise state the temperature is average room value of 25° C |
|---|---|---|---|---|
| 6 | Develop the resist image | Spray with KODAK Micro Resist Developer | 40 seconds | contact |
| 7 | Rinse the resist image | Spray with KODAK Micro Resist Rinse immediately after development | 30 seconds | |
| 8 | Dry the resist image | With a jet of clean dry nitrogen | | |
| 9 | Postbake the resist image | In a convection oven | 25 minutes | — temperature: 130° C |
| 10 | Etch the $SiO_2$ 26 forming open cathode areas 26a | By immersion in a buffered HF solution | 5 minutes | — temperature: 25° C<br>— nominal rate: 1000 A per minute |
| 11 | Rinse | With distilled deionized water (conductivity of $18 \times 10^6$ ohm - cm. Referred to below as "water") | 5 minutes | |
| 12 | Remove 30 A oxide skin | By immersion in a 5% HF solution | 10 seconds | |
| 13 | Rinse | With water | 10 seconds | |
| 14 | Dry the wafer | With a jet of clean dry nitrogen | | — immediately transfer wafer to vacuum evaporator and pump down the system |
| 15 | Deposit Cr film 28 | By electron beam evaporation | 5 minutes | — Cr (electrolytic) 99.95% pure<br>— beam current: 200mA<br>— initial rate: 100 A per minute<br>— film thickness: 420 A<br>— pressure $2 \times 10-$ torr |
| 16 | Deposit Au film 27 | By electron beam evaporation | 10 minutes | — Au 99.999% pure<br>— beam current: 250mA<br>— initial rate: 150 A per minute<br>— thickness: 1800 A<br>— pressure: $2 \times 10-$ torr<br>— vacuum not broken between Au and Cr evaporations in order to prevent oxide growth on Cr film |
| 17 | Heat treat the wafer | In a vacuum oven | 3 hours | — temperature: 250° C<br>— pressure: 0.1 torr |
| 18 | Soften the resist | IN trichloroethylene | 3 days | — temperature should not be elevated above room temperature swelling of resist must a gradual process |
| 19 | Lift off the resist | In Microstrip (TM) solvent | 2 minutes | — temperature: 98° C |
| 20 | Rinse | With water | | |
| 21 | Dry the wafer | With a jet of clean dry nitrogen | | |
| 22 | Deposit film Ag 29 | From a resistively-heated tungsten filament in a vacuum chamber | 2 minutes | — Ag 99.995% pure<br>— low tension current 5 A<br>— average rate: 2000 A per minute<br>— thickness: 4000 A<br>— pressure: $<1 \times 10^{-6}$ torr. |
| 23 | Coat wafer and continue photo- | | | — anode pattern mask (FIG. 4) |

TABLE 1-continued

| STEP NUMBER | PROCESS STEP | METHOD OR PROCEDURE | TIME | OTHER PROCESS DETAILS. Unless otherwise state the temperature is average room value of 25° C |
|---|---|---|---|---|
| | lithographic process, 3 – 9 | | | — at step 5, anode mask must be aligned to ±11μ to ensure that (after step 24) a ring of oxide isolates each cathode<br>— if alignment is unacceptable, resist is stripped and steps 3–9 repeated. |
| 24 | Etch the Ag | By immersion in KODAK Etch Bath EB-5 | 75 seconds | — temperature: 26° C ± 0.2° C |
| 25 | Lift off the resist | In Microstrip Solvent | 2 minutes | — temperature:98° C |
| 26 | Rinse | With water | | |
| 27 | Dry the wafer | With a jet of clean dry nitrogen | | |
| 28 | Remove 30 A oxide skin on back side of wafer | By swabbing with cotton soaked in 5% HF solution | 20 seconds | — extreme care is needed to prevent even HF vapours from attacking metallization on front side of wafer |
| 29 | Rinse | With water | 10 seconds | |
| 30 | Dry the wafer | With a jet of clean dry nitrogen | | — immediately transfer to vacuum evaporator and pump down the system |
| 31 | Deposit an Al film 37 | From a resistively heated tungsten filament in a vacuum chamber | 1.5 minutes | Al 99.9999% pure<br>— lown tension current 5A<br>— average rate: 2000 A per min.<br>— pressure $<5\times10^{-6}$ torr |
| 32 | Scribe the wafer | With a diamond scribing machine | | |
| 33 | Scrub the wafer | In boiling trichloroethylene | 1 hour | — Si dust and silver from scribing removed slowly from the top surface of the wafer<br>— most devices withstand simple blowing with clean, dry nitrogen.<br>— ultrasonic clear removes metallization. |
| 34 | Break wafer up into device chips | With a wafer breaking jig | | |
| 35 | Inspect each device chip | | | — visual inspection for gross defects and metaladhesion<br>— probe for shorts caused by pinholes in oxide film. |

In further explanation of the process described in Table 1, an initial silicon blank 25, for example in the form of a polished circular wafer 3.0 cm in diameter, is prepared by the CZOCHRALSKI method. The wafer is for example, of p-type silicon (boron doped), <1,1,1> orientation, of approximately 0.15 ohm-cm resistivity (doping level of $10^{17}$ per cc). Such a low resistivity, highly doped wafer is desirable to provide a common ohmic contact to the gold cathodes 27 and to the aluminum layer 37 (FIG. 2).

The polished silicon wafer is then degrased and cleaned thoroughly prior to the formation thereon of the silicon dioxide layer 26. The silicon dioxide layer 26 was grown at 1050° C in moist nitrogen (from a liquid source) in a horizontal resistively-heated furnace provided with a quartz tube and alumina liner. The silicon dioxide layer was grown to 5000 A to provide a good electrical insulation having a resistivity of, for examle, $10^{19}$ ohm-cm, between the silver anode 29 and the silicon substrate 26.

In the photolithographic process as set out in Table 1 steps (3) to (10), a mask pattern 40 (FIG. 3) is used, having darkened areas 44 where the cathodes are to occur, and having a darkened border areas 46 to define the borders of the units. The mask pattern is transferred to the photoresist layer protecting the silicon dioxide layer 26, leaving open areas in the photoresist through which etching is applied to expose the silicon substrate underneath at cathode areas 26a. A suitable etchant is hydrofluoric acid buffered with ammonium bifluoride, and ultra violet light can be used as an exposing source. The 60 mil border 46 was incorporated in the mask for alignment in the step-and-repeat electrode assembly fabrication process to make a mask which contained 100 device patterns in a 10 by 10 array.

In the second part of the fabrication process, without removing the previously applied photoresist, a layer of chromium 28, 99.95% pure and 420 A thick, and a layer of gold, 1800 A thick, is deposited by vacuum evaporation at $2 \times 10^{-7}$ torr from a hearth heated by an electron beam at a current strength of 200 milliamperes. Before insertion in the vacuum chamber, the wafer 25 is pretreated in a 5% HF solution to remove the ~30 A of silicon dioxide that forms on any bare silicon surface exposed to air.

The wafer 25 is then heated at 250° C for three hours to alloy the Si - Cr and Cr - Au interfaces and create a strongly adherent gold film. After a three day soak in trichloroethylene the photoresist is swollen and softened to such a degree that the gold film superimposed on the photoresist breaks. When the photoresist is dissolved away with an organic solvent a gold-on-chromium film is left covering all exposed silicon areas.

Figure 4:
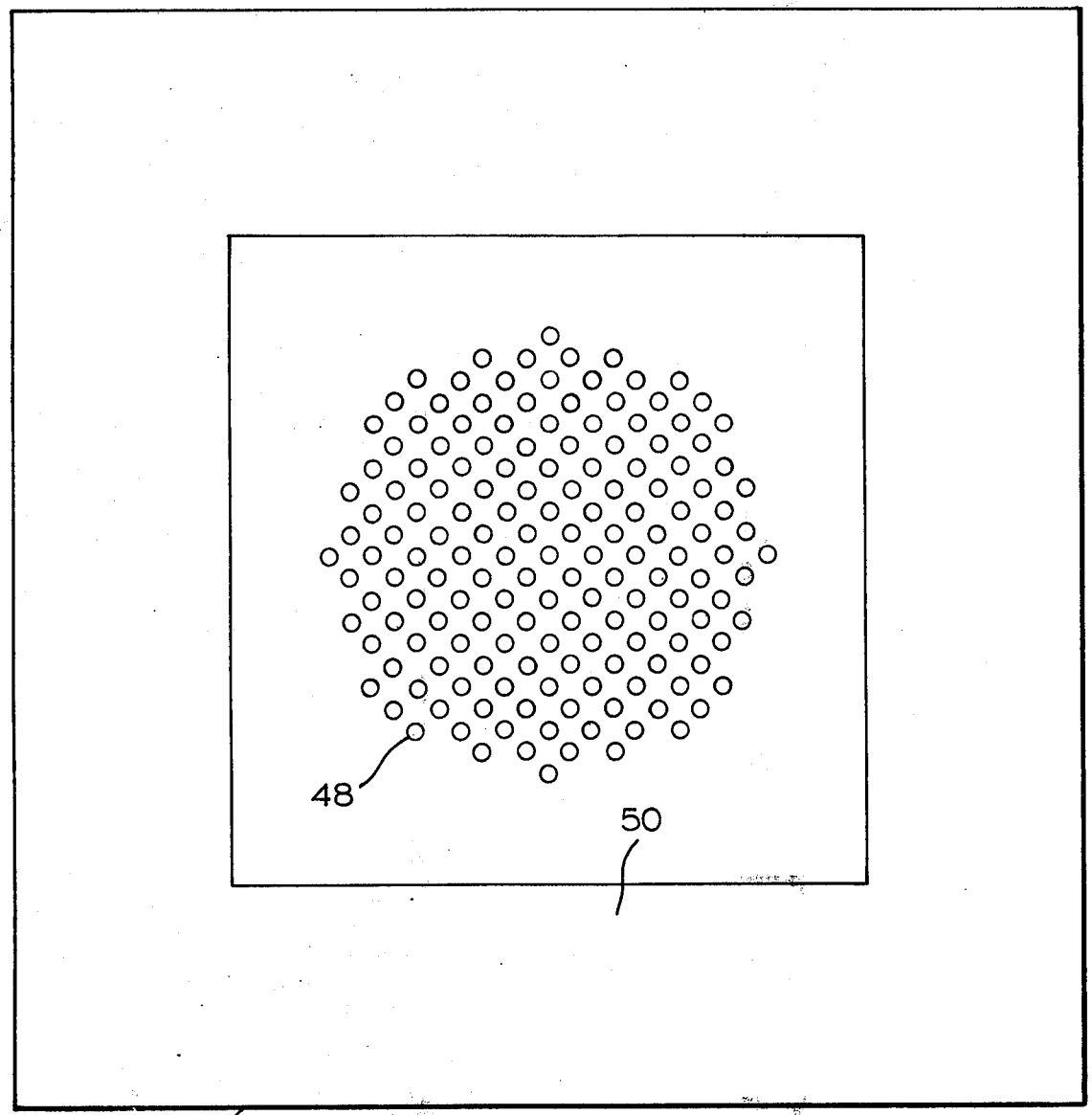
FIG. 4 shows a mode pattern mask used in fabrication of the electrode assembly of FIG. 1.

In the third part of the fabrication process, the mask pattern 42 shown in FIG. 4 is defined in the silver using a photolithographic process as set out in Table 1, (steps 23 - 25). The mask pattern 42 is clear except for darkened areas 48 which correspond to the locations at which the silver film 29 is to be etched away to create an open area, free of silver, around each cathode 27. There is also a darkened strip 50 around the perimeter of the mask 42.

Accurate alignment of the anode pattern mask 42 with the underlying cathode structure is required to ensure that each gold cathode 27 has a 10-μ-wide ring of silicon oxide isolation it from the silver anode 29. Before the silver etch (step 24 in Table 1) is carried out, the resist mask of the anode pattern is checked for good alignment. If it proves to be unsatisfactory, the resist is stripped and steps 23–25 repeated until a satisfactory alignment is achieved.

To etch 4000 A of a silver film requires about 75 seconds with KODAK Farmer's Reducer R-4A (TM). The wafer is then immediately removed from the etch bath when all the silver has been etched. The wafer is then rinsed in running distilled deionized water and thoroughly dried under clean nitrogen.

For vacuum deposited silver, as for all freshly formed metal surfaces, no surface pretreatment is required prior to resist coating. Upon removal from the silver deposition vacuum chamber, if the wafer cannot be immediately resist coated, an adsorbed water layer forms which can be removed by a 300° C bakeout for one hour in a vacuum oven.

At the beginning of the fourth part of the fabrication process the processing of the top surface of the wafer is complete. The silver has been removed from over each gold cathode and a square anode area has been defined within the alignment border of the cathode pattern mask.

In the fourth part of the fabrication process the back of the wafer is metallized to ensure a good ohmic contact to the gold cathodes 27. The 30 A of silicon dioxide always present on a silicon surface exposed to air is removed with cotton soaked in 5% HF solution. The wafer is then immediately rinsed in distilled deionized water, blown dry with clean nitrogen and placed in a vacuum coater. 3000 A of aluminum is deposited at a pressure not exceeding $5 \times 10^{-6}$ torr. An adhesion of the aluminium layer 37 to the silicon substrate 25 can be achieved which gives a contact resistance of less than 1 milliohm for the whole wafer and which results in the metallization remaining intact after the wafer is divided into one hundred chips each 1 mm square.

The finished electrode assembly dimensions are set when the wafer is scribed with a diamond scribing machine. The diamond cutting edge makes a series of parallel fissures less than 1 micrometer deep on the top surface of the wafer, first in one direction and then perpendicular to that direction. The wafer is then blown scrupulously clean of silicon dust and slivers with filtered dry nitrogen. The wafer is then broken into the one hundred chips using a suitable wafer breaking jig.

In experimental trials, the complete fabrication process set out in Table 1 represented between one and two man-weeks of work. One hundred electrode assemblies 10 were formed on a single silicon wafer, and typically between 80 and 90 of these assemblies were usable. Two to three wafers were fabricated during a typical process run.

Factors affecting the yield of usable electrode assemblies 10 obtained from one wafer include the resist adhesion, etch resistance, and resolution, mask alignment, and the effect of dust and other contaminants.

To construct the polarographic oxygen sensor hereinbefore described, an electrode assembly 10 is mounted with a conducting epoxy resin (for example having a volume resistivity of 0.0001 Ω - cm) to the copper cylinder 11. The copper cylinder 11 is then soldered to the TO-18 transistor header 13, the cylinder giving 10 mils of clearance between the electrode assembly 10 and pins of the header 13.

When the header 13 has been sealed into the brass cylinder 14 with an insulating epoxy (having a volume resistivity of for example, $4.1 \times 10$-Ω - cm) the top surface is masked and a 2 micrometer film of silver (99.99% purity) is deposited from the anode layer to the pins 19. This ensures good electrical contact between the silver anode 29 and the three anode pins 19. The ring 24 is sealed to the top of the brass cylinder 14 with contact cement to prevent any electrochemical reaction between the electrodes and brass surfaces wet by the electrolyte 23.

The reference electrode for providing electrical continuity between the electrolyte 23 (FIG. 11) of the sensor and the anode lead 19 comprises the silver anode 29 coated with a porous layer of silver chloride (indicated at 52 in FIG. 2). Such an Ag/AgCl electrode is reversible to chlorine ions. When immersed in a solution containing chlorine ions and when acting as an anode, chlorine ions combine with silver to form AgCl: when acting as a cathode, chlorine ions pass into solution from the AgCl layer thereby depleting it.

The Ag/AgCl electrode surface 52 of the sensor is prepared by electroforming an AgCl layer on the silver anode 29. This is achieved by immersing the silver layer in a saturated KCl solution and biasing the silver layer at +0.20 volts for several seconds with respect to a stainless steel cathode. The AgCl layer should be about 500 A thick.

The electrolyte 23 forms a salt bridge between the gold cathodes 27 and the silver anode 29 and consists of a buffered 0.5 N KCl solution (pH 10.4).

The gas permeable membrane 12 is between 0.00625 and 0.254 mm in thickness and is positioned over the electrode assembly 10 and held in place by the rubber O-ring 22. Other membrane materials, such as polypropylene, may also be used to form the membrane 12. The diffusion zone between the gold cathodes 27 and the gas-permeable membrane 12 is stabilized against mechanical pressure by an additional membrane of cellophane (TM), 0.25 mm thick which has been saturated with electrolyte..

Figure 5:
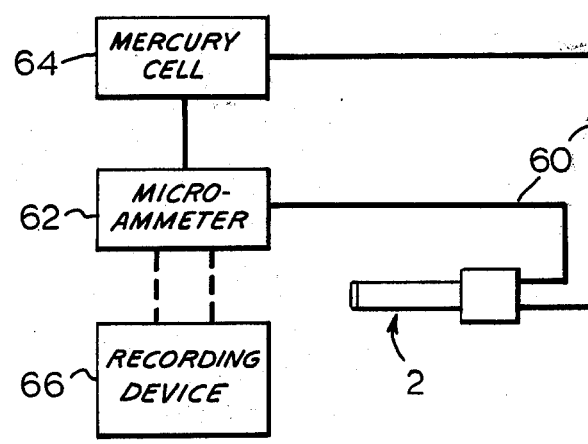
FIG. 5 shows a circuit arrangement for the sensor of FIG. 1.

Shown in FIG. 5 is a circuit arrangement for the sensor 2. The sensor 2 is connected by means of a cable 60 to a high impedance micro-ammeter 62. A polarizing voltage is supplied by a mercury cell 64 and is made adjustable from zero to 1.35 volts by means of a potentiometer. A recording device 66 can be connected to the ammeter if desired.

A series of tests have been performed on a polarographic oxygen sensor fabricated as hereinbefore described. The sensor was inserted in the specially designed cuvette during the course of the tests to standardize test conditions. The volume of fluid flowing through a conduit of the cuvette from inlet to outlet was 0.5 ml and the sample flow rate could be varied from zero to 36 ml/min. The temperature of the thermostatted fluid within the cuvette was monitored constantly and found to be stable to within 0.10° C for the range 20° to 40° C.

The cuvette employed was disposed within a large water bath which allowed a good circulation of water at constant temperature. The water was in direct contact with the sample conduit, the cuvette, and the sensor. The conduit and the cuvette were made of brass facilitating an even temperature distribution.

Using a micro-thermometer with a resolution of 0.05° C, measurements were made to determined the variation of temperature throughout the cuvette when sample fluids were flowing. It was found that the maximum temperature differences were around ± 0.1° C.

Different oxygen partial pressures in the fluid samples were obtained by equilibrating solutions in a jacketed flask (immersed in the constant temperature bath) with different oxygen fractions, $FO_2$ of 0.05, 0.10, 0.21, 0.70 and 1.00. Equilibration of a 50 ml sample was completed after 30 minutes. The following results were observed.

Residual Current

The current for $Po_2 \simeq 0$ mm Hg (the residual current) was measured by injecting a sodium sulphite solution in 2% borax into the sample fluid space and waiting three hours before recording the current. It should be noted that the seal between electrode and reducing solution was airtight to prevent contamination with ambient air.

The residual current was found to be less than $3 \times 10^{-11}$ amperes. When using $N_2$ or water as the sample fluid, the residual current was slightly higher but never more than the equivalent of 0.2 mm Hg $Po_2$ so that in most cases, a calibration line of a calibration graph of the sensor could be assumed to pass through the origin.

Calibration

Figure 6:
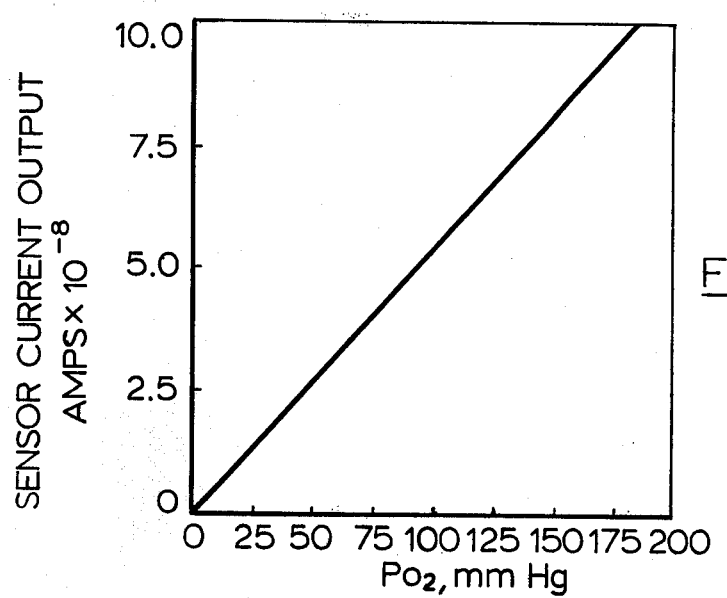
FIG. 6 is a graph of the FIG. 1 sensor current output as a function of the oxygen partial pressure of a sample fluid.
Figure 7:
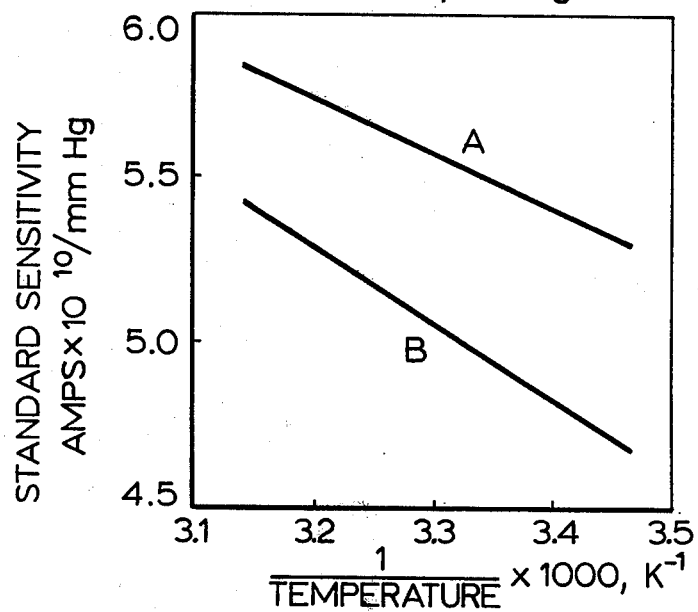
FIG. 7 is a graph of standard sensitivity of the FIG. 1 sensor as a function of temperature for two different sensor membranes.

A calibration curve for the sensor was derived from a series of readings of sensor current output at specific oxygen partial pressure. A calibration curve for measurements made at 37° C is shown in FIG. 6.

The current output of the sensor was dependent on the time of immersion in the sample fluid. Introduction of a 2 ml liquid sample into the cuvette containing the sensor resulted in a maximum current reading within 7 seconds, without current decay for at least 30 seconds regardless of the oxygen partial pressure. The reading obtained with a static gas sample was stable for at least 30 minutes.

Early decay of the current reading was observed with all liquids. Following the plateau, the percentage decay over a 30 minute period was 26% for distilled water and 29.5% for 20% glycerine in water.

A consistently higher current signal was obtained for gas then for water and glycerine in water at identical $Po_2$ with both Teflon FEP (0.0254 mm) and polypropylene membranes (0.0125) and 0.0254 mm). Results also indicated that sample fluid flow reduces the difference between the fluid and gas readings to less than 1% of the gas current output.

Sensitivity

The sensor sensitivity was expressed as follows:

$$\sigma^T = \frac{i_m - i_{res}}{Po_2}$$

where
$\sigma^T$ = sensitivity at temperature T (° C) in amperes/mmHg $Po_2$
$i_m$ = measured current (amperes)
$i_{res}$ = residual current (amperes)
$Po_2$ = partial pressure of oxygen in the fluid sample (mmHg) calculated from the barometric pressure, $P_B$, the water vapor pressure, $P_{H_2O}$ at temperature T (° C) and the fraction of $O_2$ in the equilibrating gas, $Fo_2$:

$$Po_2 = (P_B - P_{H_2O}) \times Fo_2$$

Since the ratio $i/Po_2$ often varies over the $Po_2$ pressure range from zero to one atmosphere, it is convenient to define a standard sensitivity, $\sigma_s$, by the $i/Po_2$ ratio obtained for water in equilibrium with ambient air at a specified temperature and pressure, i.e.

$$\sigma_s = \frac{i}{Po_2} \bigg| Fo_2 = 0.21$$

The standard sensitivity (at 37° C) of the sensor tested can be calculated from the calibration graph of FIG. 6 and is equal to $5.55 \times 10^{-10}$ amperes/mmHg $Po_2$.

Temperature Dependence of Sensitivity

The effect of temperature on sensitivity of a membrane-covered electrode is the combination of the temperature influence on the rate of $O_2$ transfer through the sample, membrane and electrolyte and on the rate of $O_2$ reduction at the cathode surface.

An increase in temperature enhances transfer through the membrane as well as the electrochemical reaction at the gold cathodes; however, transfer of oxygen through the electrolyte layer is delayed since the $O_2$ solubility coefficient in the electrolyte decreases by a greater amount than the increase in diffusion coefficient. The data collected in the experiments revealed an increase in sensitivity with a rise in temperature which indicates that membrane transfer and the electrochemical reaction over-ride the influence on solubility. Polypropylene is more susceptible to temperature variation than Teflon FEP (TM) as is shown by the curves of sensitivity as a function of temperature shown in FIG. 7 where curve A is for a Teflon FEP (TM) membrane and curve B is for a polypropylene membrane. Both membranes had a thickness of 0.0125 mm. Thus, at a given temperature the number of gas molecules activated sufficiently to diffuse through the membrane was found to be smaller for polypropylene than Teflon FEP (TM). In terms of sensor sensitivity, less current per mm Hg $Po_2$ will be recorded when using polypropylene; however, sensitivity changes caused by temperature variations in the biological range are more prominent for polypropylene.

Figure 8:
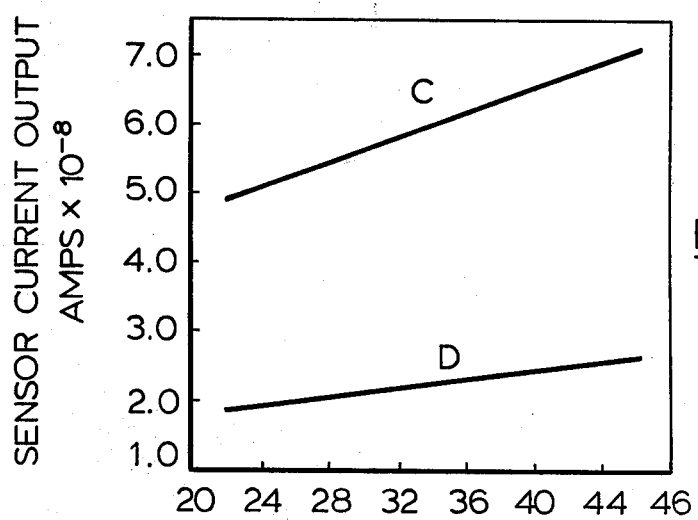
FIG. 8 is a graph of the FIG. 1 sensor current output as a function of temperature at two oxygen partial pressures.

Shown in FIG. 8 is the effect of temperature on the sensor output current at $Po_2 = 147$ mmHg (Curve C) and at $Po_2 = 43$ mmHg (Curve D). The temperature coefficient for the sensor output was found to be 1.8%/° C at $Po_2 = 43$ mm Hg and only 2.0%/° C at $Po_2 = 147$ mm Hg.

Linearity

The linearity of sensor response to a slow change in $Po_2$ was assessed by calculating the ratio $\sigma Fo_2/\sigma s$, where $\sigma Fo_2$ is the sensitivity at a given $Fo_2$. In addition, the percentage deviation from linearity can be expressed by:

$$\Delta\% = \frac{\sigma Fo_2 - \sigma_s}{\sigma_s} \times 100$$

The standard sensitivity, $\sigma s$, was generally greater than the sensitivity obtained with higher oxygen partial pressures (e.g. $Fo_2 = 0.70$). This phenomenon was of comparable magnitude for both the Teflon (TM) and the polypropylene membranes and was found to be independent of both the polariziing voltage (0.6 to 1.0 volts) and temperature (25° to 40° C).

Setting the sensor zero with water in equilibrium with ambient air resulted in a deviation from linearity at high $Po_2$ (covering a 3-fold increase to $Po_2$) of from 0.8 to 1.3%. The standard error of the measurement varied little over a period of 3 days, ranging from 0.05 to 0.15% of the standard sensitivity.

Various other materials can be used in addition to those detailed above.

Silver is a preferred anode metal in the described sensor because the Ag/AgCl reference electrode possesses excellent reversibility and reproducibility at the low currents drawn from the cell, as well as good long term stability. Previous studies have shown that the Ag/AgCl electrode is probably the most reproducible electrode (excepting the hydrogen reference electrode) as well as being a reliable and convenient reference electrode. The adhesion of silver to silicon diode is adequate for the described electrode assembly structure and thin films of silver can be very precisely etched. Since silver has a valence of +1 and the Ag/AgCl reference is reversible to chlorine ions, Faraday's Law requires a silver film 2 $\mu$ thick to give the device a lifetime of 100 hours at a continuous $Pi_2$ of 150 mm Hg. However, thin film fabrication can reduce the bulk cost so drastically from that of a conventional sensor that a disposable sensor is feasible.

When a silver-silver chloride electrode is used, the cathodes must be biased to between −0.4 and −0.8 volts to operate in the diffusion limited mode, so that the current will be directly proportional to $Po_2$, giving a linear calibration line of current versus $Po_2$. However, by suitable choice of a reference electrode which maintains itself approximately −0.5v with respect to the oxygen cathode, the need for a polarizing voltage (i.e. battery) is eliminated (at least in a sensor intended only to measure oxygen partial pressure). A suitable reference electrode is a solid at ordinary temperatures, and its anode film products have both a low solubility and a low resistivity; it should preferably form the oxide of the metal, rather than the salt of the anion in the electrolyte; it should of course, produce relatively stable potential for long periods of time and not plate at the oxygen cathode under conditions required for reduction of oxygen. An adequate adhesion of the reference electrode material to silicon dioxide is also desirable.

Iron, zinc, cadmium, indium and chromium can be used as such a suitable reference electrode. Other suitable materials may also be used. Cadmium, chromium and indium are preferably used, as not only do these metals provide the required constant voltage at which oxygen could be reduced spontaneously, but the predominant feature of the anode process, for each metal appears to be an oxide or hydroxide formation. The corresponding required electrolyte does not affect the useful life of the sensor.

If it is desired to increase the operational life of the sensor, the amount of anode metal may be increased. This can most easily be accomplished by plating up the thickness of the anode electrode after the selective metal etch to define the anode pattern.

Very high purity gold is preferably used for the cathode metal because it gives more reproducible results than does platinum or ay other noble metal. The well known "poisoning" effect with plantinum electrodes, which after a period of time affects the calibration of the device, has not been observed with use of the gold electrodes. In addition, gold gives a wide, flat plateau when used to obtain a current-voltage curve for the sensor, indicating a relatively large hydrogen overvoltage. This broad horizontal plateau is desirable since it permits stability of the calibration line, both the reference voltage and bias voltage varying in response to environmental changes. To achieve long-term stability at 99.999% purity gold was used for the cathode metal.

Gold is suitable for high-resolution forming and since, in the approach described here, the electrode is supported by a silicon substrate, the low mechanical strength of gold is not itself a problem.

For less demanding applications of the sensor where long term stability is not crucial, platinum or other noble metals can be used as the cathode metal in the place of gold. If the electrolyte buffer is adjusted to very basic levels (ph 10), nickel can serve as the cathode metal. This would reduce materials and fabrication costs, especially if the nickel layer is selectively plated on exposed silicon (here, the oxide acts as a "plating mask"). A lower purity gold layer can be plated on the exposed silicon or a platinum layer deposited from platinum silicide, again using the oxide as a mask.

There are further metal-electrolyte couples that can sense oxygen at one of the electrodes. Lead-silver is one of the more attractive choices. Both metals can be easily formed and etched and are more economical to use than gold or platinum.

Silicon is advantageously used for a supporting substrate of high conductivity since its technology is well developed, and it has good mechanical strength. The use of a silicon substrate is also compatible with the integration of a preamplifier (or complete electronics and signal processing circuitry) on the same substrate as the electrode assembly 10. Such a preamplifier would minimize sensor lead capacitance, stray capacitance, and noise pickup, reduce drift in the signal conditioning, and facilitate temperature compensation since the thermal conductivity of silicon is good. Thermistor or p-n junction temperature sensors incorporated on the same substrate can closely track the temperature of the oxygen sensor.

The selection of silicon dioxide for inter-electrode insulation is advantageous from both an electro-chemical standpoint and processing considerations. Unpurified silicon dioxide (fused quartz) has been used extensively as an electrode insulation material. Silicon dioxide provides extremely high anode to cathode leakage resistance giving rise to a very small residual current (at zero $Po_2$). In addition it is one of the few insulating materials which can be formed in thin uniform films and controllably etched using planar photoresist techniques which enable tolerances of $\pm 1\mu$ to be achieved. Insulating films of silicon dioxide possess good mechanical properties and a very low thermal impedance and are therefore attractive from the standpoint of sensor fabrication.

Other suitable materials are ceramic ($Al_2O_3$) or dielectric crystals (e.g. ruby, sapphire), dense plastics, glasses and even membranes of, say, Teflon, silicone, mylar and the like. If a film of a noble metal can be applied to the substrate, then the oxygen sensor design can be achieved for that substrate. (For other uses, e.g. as a pH sensor, noble metals need not be used). An insulating layer is then applied in order to electrically and physically isolate the anode from the cathodes. This layer must have a high resistivity ($10^{13}$ ohm-cm) and be uniform and pinhole-free, so that leakage currents do not degrade the output current sensitivity of the device. The insulator can be, for example, silicon dioxide (sputtered as SiO or as Si and thermally oxidized) or anodized aluminum or tantalum (Al or Ta sputtered or evaporated and then anodized to $Al_2O_3$ or $Ta_2O_5$).

Such substrates can reduce materials cost for the sensor since silicon wafers remain somewhat expensive. Moreover, for certain applications, the choice from such a wide range of materials will allow greater freedom in sensor configuration and integration with a system package.

Aluminum is a widely used metal for electrical contacts in semiconductor work because of its excellent adhesion properties, high conductivity and precision etch characteristics.

A disadvantage of previous polarographic $O_2$ sensors is their use of a liquid electrolyte. The membrane is preferably sealed over the electrolyte in such a way that the electrolyte layer is isolated physically and chemically from the exterior medium to be sampled. Advantageously, according to the present invention, electrolyte salts can be vacuum evaporated over the sensor face through a metal mask so that a dry electrolyte layer is formed on the sensor's electrode metallization. After the membrane is applied, the sensor remains completely inactivated since no liquid electrolyte is present to allow ionic conduction. The shelf life of the sensor is indefinite, provided that it is stored in a dry atmosphere (25% humidity). Examples of suitable electrolyte materials are KCl, HCl with sodium borate and boric acid as a buffer.

The sensor can subsequently be activated by placing it in steam for several sec. This causes water vapour to pass through the hydrophobic membrane and create a thin, liquid electrolyte film on the inside surface of the membrane. For biomedical applications, the sensor can be autoclaved at 134° C for 2 minutes, thereby achieving both activation and sterilization.

In addition to Teflon (TM) or polypropylene membranes, other gas permeable polymer membranes may be used. Among the suitable membrane materials are silicone, collodion, various forms of rubber, polystyrol, and polypropylene.

Figure 1:
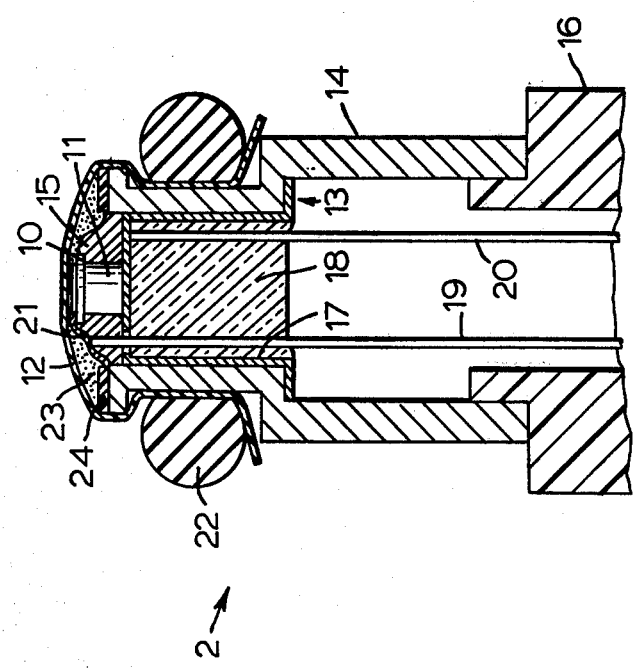
FIG. 1 is a longitudinal section through a sensor according to the invention.

A disadvantage of the FIG. 1 membrane 12, and of any membrane which is stretched over the electrode assembly and clamped at its edges, is that it is particularly prone to uneven stretching and compression across its surface. These lead to variations in membrane characteristics and sensor output.

According to the invention, therefore, the membrane 12 may be applied as one of the fabrication process steps, on the surface of the sensor wafer after deposition of an electrolyte layer. Specifically, membranes of high quality may be formed directly on the wafer in vacuum during or after the application of electrolyte. A monomer gas, such as propylene gas, may be introduced into the chamber, allowed to adsorb onto the surface of the electrolyte, and then polymerized by the application of energy. For example, the polymerization of a monomer gas introduced into the vacuum chamber may be accomplished by irradiation of the substrates with a plasma glow discharge, or intense radiation from an electron beam or X-ray source. The membrane layers so formed are thin ($1\mu$), uniform, crystalline, and adhere tenaciously to all exposed surfaces. The buffered electrolyte may be codeposited with the membrane to form a gel or porous layer support for the membrane.

According to the invention, a porous film (such as a gel or porous plastic membrane saturated with electrolyte and then dried) may be formed or bonded over the sensing surface. The porous plate membrane provides a uniformly thick mechanical backing to the gas permeable outer membrane without in any way increasing the diffusion resistance to oxygen of the electrolyte layer. An example of a suitable such film is cellulose or polystyrene.

Figure 9A:
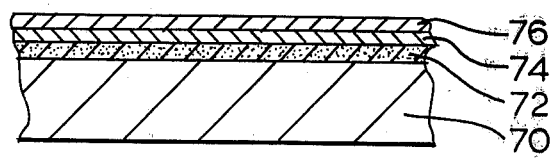
FIGS. 9a to 9c are cross-sectional views showing an alternative method of fabrication of an electrode assembly for use in the FIG. 1 sensor.
Figure 9B:
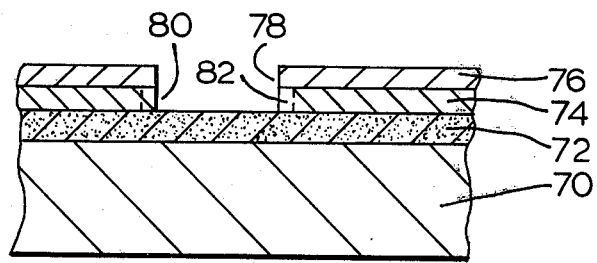
Figure 9C:
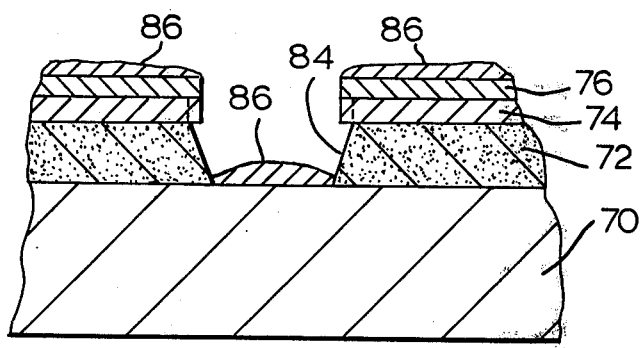

The electrode assembly fabrication process described with reference to Table 1 can be simplified by use of a self aligning mask process if the anode metal can be anodized in a thin surface layer that will resist the action of the silicon dioxide etchant. For example, chromium, cadmium, indium and silver possess suitably thin anodization layers such that a self aligned etch mask can be formed. This electrode assembly fabrication process is illustrated in FIGS. 9a, 9b, 9c and it is carried out as follows.

1. A silicon wafer 70 is selected and a layer 72 of silicon dioxide is grown thereon, typically 3,000 A thick. An anode metallization layer 74 (for example silver) is then deposited on the entire surface of the layer 72 as in step 22, Table 1.

2. A negative photoresist layer 76 is applied over the anode metallization layer 74 and exposed and then developed to leave areas 78 (FIG. 9(b)) of no photoresist where the cathodes are to be located.

3. The anode layer 74 is then etched, using a suitable photoresist mask, to provide holes 80 in the anode layer 74 at the location of the cathodes.

4. The walls of the holes 80 are then anodized, forming an anodized ring 82 around each hole. (For example, when the anode is silver, the anodization ring is silver chloride).

5. The silicon dioxide layer 72 is then etched, using the photoresist layer 76 and the anodized ring 82 as an etch mask. This forms holes 84 (FIG. 9(c)) in the silicon dioxide layer, which holes extend down to the silicon substrate 70.

6. The cathode metallization (e.g. gold) is next applied over all top surfaces, as indicated at 86 in FIG. 9(b). When the cathode metallization is evaporated from a heated filament, it will not deposit on the walls of hole 84.

7. The process is then completed by lifting off the negative photoresist layer 76, carrying with it the metallization 86 over the anode layer 74. The cathode metallization, being applied directly to the silicon (a layer of chromium may be applied prior to the gold to improve adhesion) remains in place.

The sequence of operations just described eliminates use of the mask shown in FIG. 4 with all the attendant steps. Specifically, mask alignment problems are avoided and the 10μ ring of exposed silicon dioxide is functionally replaced by a circular step (typically 3,000 A in height) of silicon dioxide between each cathode and the anodized anode material. The self alignment process permits a greater packing density of anode-cathode pairs. Devices with improved performance characteristics may therefore be fabricated on even smaller areas of silicon.

Figure 10:
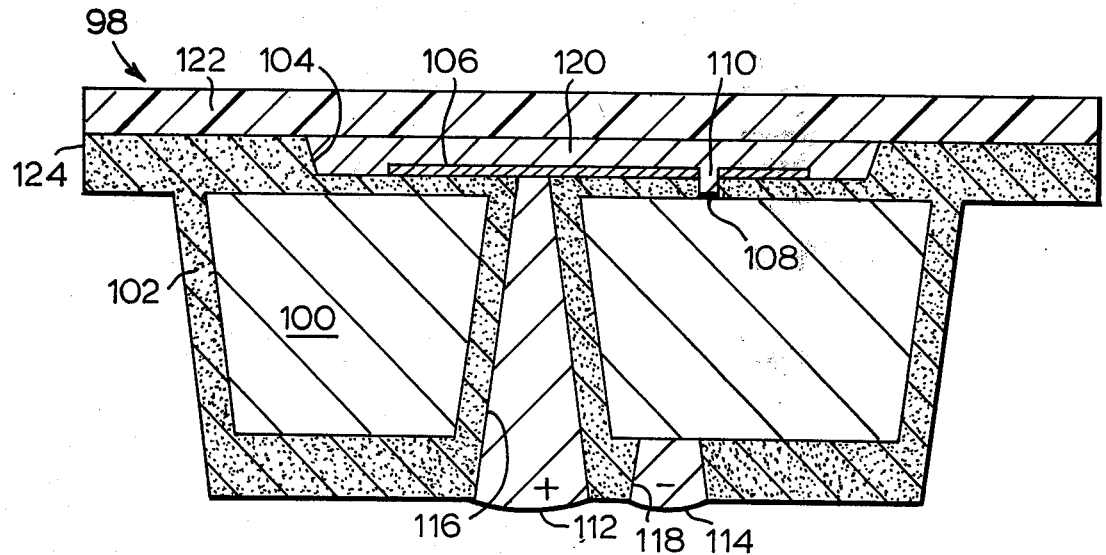
FIG. 10 is a cross-sectional view showing another sensor according to the invention.

Reference is next made to FIGS. 10 to 20, which show an alternative embodiment of the invention. In FIG. 10, there is shown a form of sensor 98 produced on a silicon wafer 100. The wafer 100 is enveloped in a layer of silicon dioxide generally indicated at 102. The silicon dioxide layer 102 has a well or hole 104 formed in its top surface. Located in the well 104 is an anode layer 106, with cathodes, one of which is diagrammatically indicated at 108, located in holes 110 therein and in contact with the silicon substrate 100. It will be appreciated that the thickness of the sensor shown in FIG. 10 is very much exaggerated for illustrative purposes, and that in reality the diameter of the sensor 98 is between 10 and 20 times its thickness. For example, the finished sensor 98 may be 5 millimeters in diameter and 0.25 millimeters thick.

A distinguishing feature of the sensor 98 is that its anode and cathode contacts 112, 114 are "punched" through holes in the bottom of the sensor. Specifically, the anode metallization contact 112 is located in a hole 116 in the silicon wafer 110 and silicon dioxide layer 102 and extends to the bottom surface of the anode metallization layer 106. It will be noted that the anode contact 112 is completely insulated from the silicon wafer 100 by the enveloping silicon dioxide layer 102.

Similarly, the cathode contact 114 is located in a hole 118 in the silicon dioxide layer 102 and extends to and contacts the silicon wafer 100. The contacts 112, 114 are insulated from each other by the silicon dioxide layer 102 between them.

The sensor 98 further includes a buffered electrolyte 120 located in the well 104, and filling the well approximately to its top. The entire top surface of the sensor 98 is covered by a gas permeable membrane 122, formed from one of the membrane materials previously described. The sensor 98, which may be circular, square, or of other desired shape in plan, typically includes an encircling flange 124 which facilitates placement of the sensor unit in an appropriate holder.

The method by which the sensor 98 is formed will next be described, with references to FIGS. 11 to 20.

Figure 11:
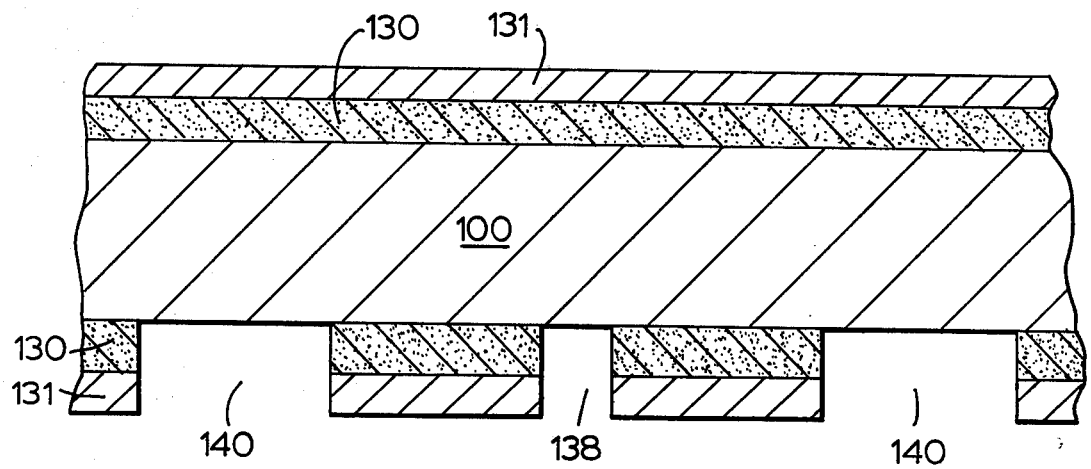
FIG. 11 is a cross-sectional view showing a wafer in an initial stage of fabrication to produce the FIG. 10 sensor.

Firstly, with reference to FIG. 11, the silicon wafer 100 is selected, and a layer of silicon dioxide 130 (typically 7000 A thick), is grown on both sides thereof. The wafer 100 is then coated with negative photoresist 131 on both sides, and then the back of the wafer is exposed through a mask such as those shown at 132 or 132' in FIGS. 12 or 13. The top surface of the wafer is exposed fully, with no mask, so that it will be fully protected by the photoresist.

Figure 12:
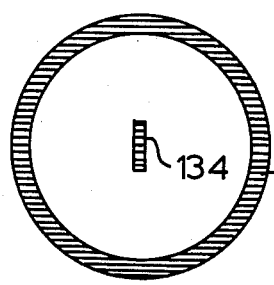
FIGS. 12 & 13 show alternative masks used in the fabrication of the FIG. 10 sensor.
Figure 13:
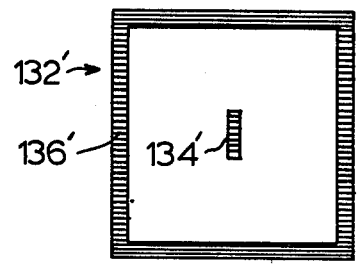

The masks 132, 132' shown in FIGS. 12 and 13 include darkened areas 134, 134' where the anode contact 112 is to be punched through. The masks 132, 132' also include a darkened peripheral area 136 or 136' which defines the edge of the finished sensor unit (where the flange 124 is located).

The photoresist layer 131, is next developed, leaving an open area 138 in the bottom photoresist layer 130 for the anode contact 112, and an open rectangular or ring shaped area 140 for the edge of the finished sensor. The exposed silicon dioxide is etched using a buffered hydrofluoric acid etchant. This extends the open areas 138, 140 through the silicon dioxide layer 130 down to the silicon wafer 100.

Figure 14:
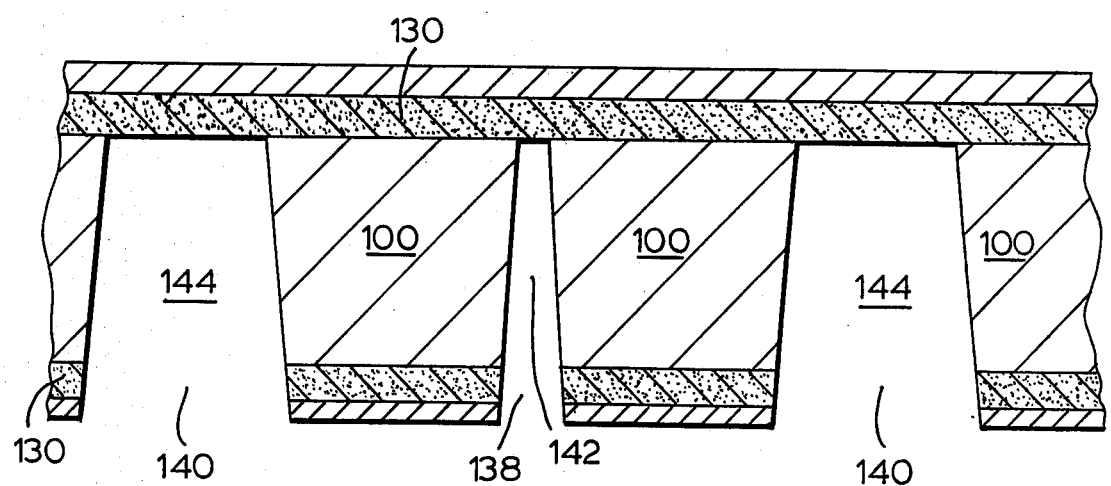
FIGS. 14 & 15 are cross-sectional views showing still further stages in the fabrication of the FIG. 10 sensor.
Figure 15:
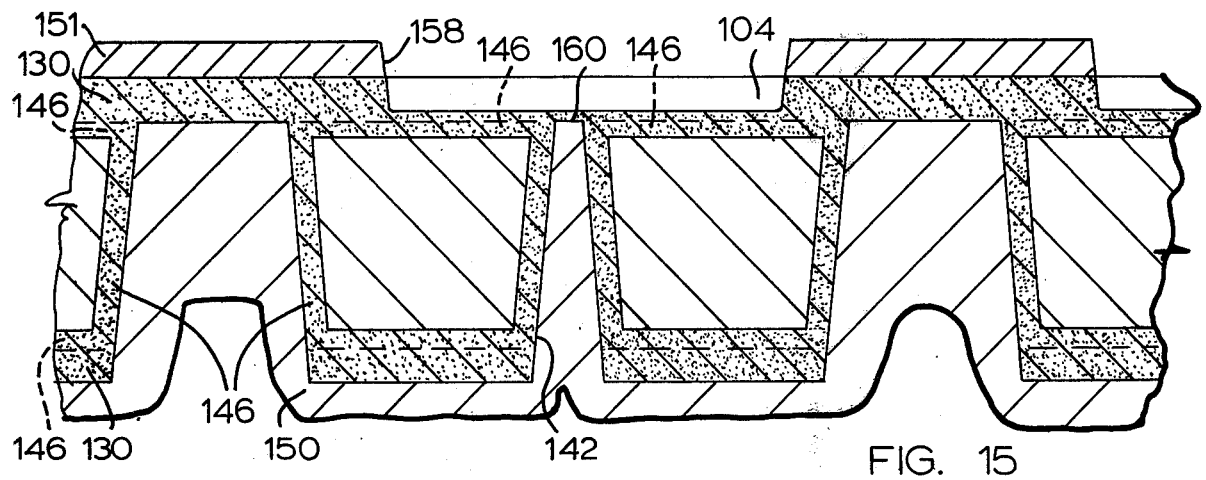

The next step, as shown in FIG. 14, is to employ an isotropic silicon etch to remove silicon unprotected by the silicon dioxide layer 130. In other words, the silicon 100 at the location of open areas 138, 140 is removed. The entire thickness of silicon exposed through the open areas 138, 140 is removed, as far as the top silicon dioxide layer 130. The apertures in the silicon 100 formed by this process are shown at 142, 144 in FIG. 14.

After completion of the steps described in connection with FIG. 14, the photoresist layers 131 are removed, and the wafer 100 is returned to the furnace, and an additional 3000 A layer 146 (FIG. 15) of silicon dioxide is formed at all locations where silicon existed previously. It will be seen from FIG. 15 that the areas where layer 130 was undisturbed by the hydrofluoric acid etch now have a layer 10,000 A thick of silicon dioxide, while the remaining areas (the walls of openings 142, 144) have a 3,000 A silicon dioxide layer thereon. The two layers 130, 146 together form the silicon dioxide layer 102.

Figure 16:
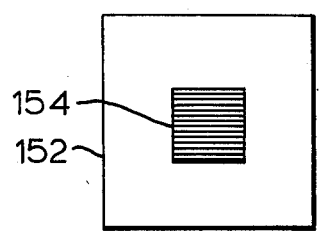
FIG. 16 shows a mask used to produce a well in the FIG. 10 sensor.
Figure 17:
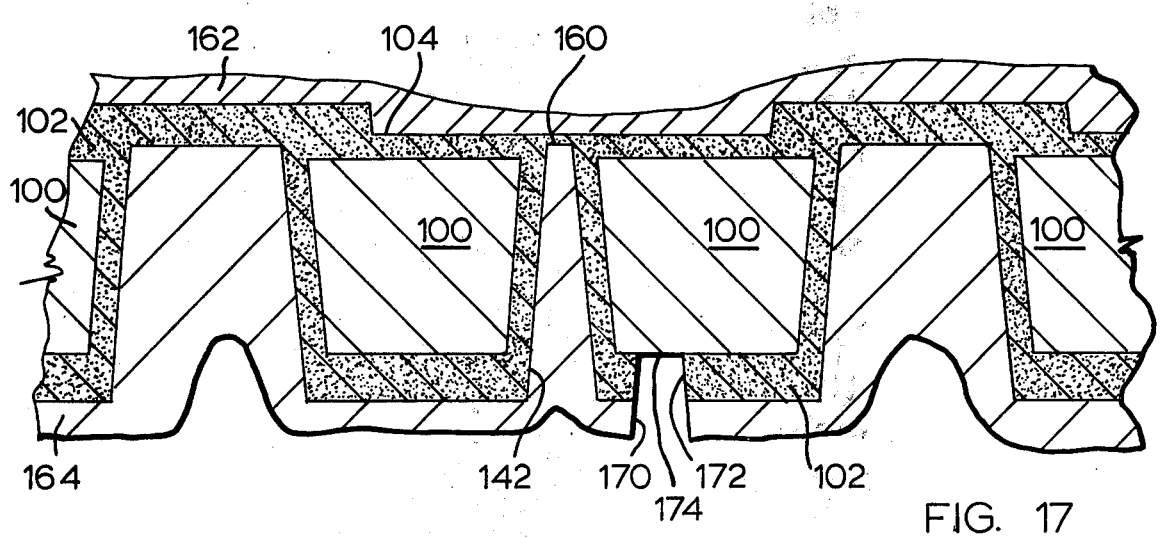
FIG. 17 is a cross-sectional view showing a further stage in the fabrication of the FIG. 10 sensor.

The entire bottom surface of the unit so far described is next coated with photoresist and fully exposed (not through a mask) to create a developed photoresist layer 150 (FIG. 15) which protects the bottom surface of the wafer. The top surface of the unit is coated with photoresist 151 and exposed to light through a mask 152 as shown in FIG. 16. The mask 152 has a darkened area 154 which defines the well 104 in which the electrode structure is to be located. The top photoresist layer 151 is then developed and the unexposed photoresist is then removed, leaving an open area 158 therein. Approximately 6500 A of silicon dioxide are etched from the top surface, through the opening 158, thereby forming the well 104. It will be seen that since the top silicon dioxide layer 130 was 7000 A thick over the openings 142, 144, this leaves a layer 160 of silicon dioxide about 500 A thick between the well 104 and the top of the opening 142.

Figure 18:
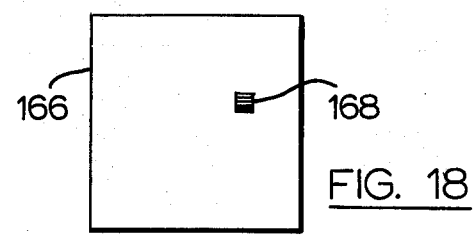
FIG. 18 shows a mask used in the fabrication of a cathode contact for the FIG. 10 sensor.
Figure 19:
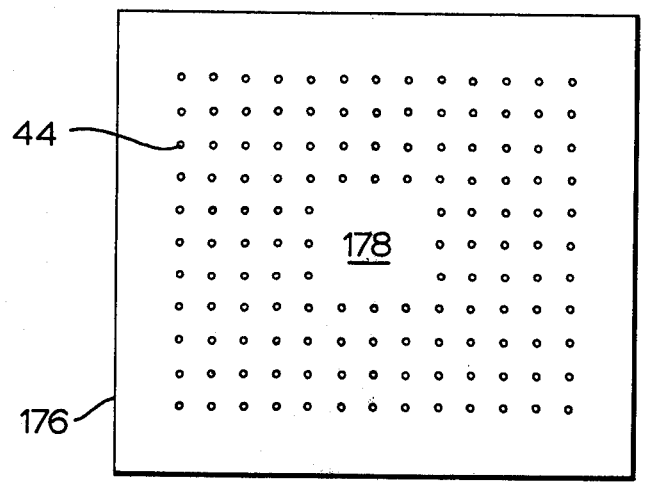
FIG. 19 shows a cathode pattern mask for the FIG. 10 sensor.

The exposed photoresist layers 150, 151 on the top and bottom of the unit are next removed, and a fresh photoresist layer 162 is applied to the top of the unit, exposed, and developed, resulting in a layer 162 (FIG. 17) which protects the top surface of the unit. A photoresist layer 164 is applied to the bottom of the unit and is exposed through a mask 166 as shown in FIG. 18. The mask 166 has a darkened area 168 so as to leave an unexposed area at the location of the cathode contact 114. The unexposed photoresist is removed, leaving an opening 170 (FIG. 17) and the unit is etched through opening 170 to remove the approximately 10,000 Å thick layer of silicon dioxide at the location of the cathode contact. The resultant hole 172 in the silicon dioxide exposes surface 174 of the silicon substrate 100 for application of the cathode contacts.

At this stage, before the photoresist layers 162, 164 on the top and bottom of the unit are removed, the unit is placed in a pretreatment solution to activate the exposed silicon surface 174. The unit is then placed in an electroless nickel bath (not shown) which deposits nickel on the exposed silicon surface 174 to form the cathode contact 114 as shown in FIG. 10. The nickel is plated up to the surface of the silicon dioxide layer 102, i.e. approximately 10,000 Å thick. Then for ease of making contact to the cathode contact 114, a thin layer of gold (not shown) may be deposited on the entire bottom surface of the unit. The photoresist layers 162, 164 at the top and bottom of the unit are then removed, taking with them the gold metallization except that over the cathode contact 114.

After the cathode contact 114 has been formed and layers 162, 164 removed, the electrodes (namely the anode 106 and the cathodes 108) are formed in the well 104, using either the steps described in Table 1, or the alternative procedure described employing the self-aligning mask and the anodized anode layer. The mask 176 (FIG. 19) employed to form the cathodes is modified from that shown in FIG. 3 to provide an area 178 in which no cathodes are formed. Area 178 is at the location of the anode contact 112, since it would be undesirable to have any cathodes contacting the anode.

After the electrodes 106, 108 are formed, the next step is to subject the back of the unit to a 500 Å silicon dioxide etch. This removes the silicon dioxide layer 160 at the top of the opening 142 for the anode contact, thereby exposing the anode metallization 106 from the back of the unit through the opening 142.

After this has been completed, a battery contact is made from above the unit to the anode metallization layer 106, and the anode metallization layer 106 is used to form one electrode for the electroplating of the anode contact material (typically silver) to fill the hole 142 to a level flush with the level of the silicon dioxide 130. To ensure that the top surface of the unit is not plated, only its back surface is exposed to the plating solution (which forms the second electrode required for electroplating).

Figure 20:
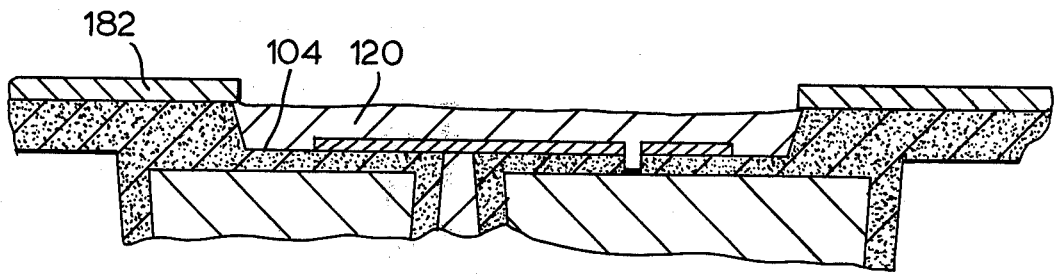
FIG. 20 is a cross-sectional view showing a still further stage in the fabrication of the FIG. 10 sensor.

After the completed unit is formed as described, a metal mask 182 shown in FIG. 20 (and which is the inverse of the mask shown in FIG. 16) is placed on the unit, to expose the well 104 while protecting the remainder of the top surface of the unit. The electrolyte 120, for example a dry buffered electrolyte layer, may then be vacuum deposited (or applied in any other suitable manner) into the well 104 to fill the well flush with its upper surface. After this has been completed, the mask is removed and the gas permeable polymer membrane 122 is applied over the entire top surface of the unit using the methods previously described. Alternatively, and as previously described, a dry porous polymer may be co-deposited with the electrolyte to yield a porous polymer structure saturated with the electrolyte and which provides mechanical backing for the gas permeable membrane.

The completed unit is then placed up-side-down on a curved glass surface, and application of slight pressure fractures the unit at the locations of the open areas 144 at the periphery of each sensor unit. This causes controlled automatic release of the individual sensor units. The sensor units so released are completely encapsulated by the silicon dioxide layer 102 and by the membrane 122 over their top surfaces, with the anode and common cathode contacts 112, 114 located on their bottom surfaces for circuit interconnection.

It will be appreciated a structure of the kind shown in FIG. 10, in which the electrodes are located in a well, and in which the anode and cathode contacts are made through holes in the back of the silicon wafer, may be made by means other than the specific steps just described. In addition, the rear contacts can be made without necessarily placing the electrodes in a well although the well is much preferred.

The invention has been described primarily with reference to its use as an oxygen sensor. However, it will be appreciated that depending on the materials used for the cathodes and anode, numerous other applications of the invention are possible. For example, the gold electrodes may be replaced by antinomy electrodes to form a pH sensor. A reference electrode will still be required and the silver-silver chloride electrode is suitable for this purpose. A dry electrolyte layer may be deposited as before, for example saturated potassium chloride. The gas permeable membrane can now be replaced by an ion exchange membrane permeable to hydrogen or hydroxyl ions or merely by a porous membrane which acts as a filter.

The presence of a variable oxygen partial pressure in the pH sensor will introduce a substantial uncertainty in the pH reading, depending on the particular oxygen partial pressure present. This variability can be compensated for by fabricating an oxygen sensor in conjunction with the antimony pH sensor, and connecting the oxygen sensor in known fashion to provide a correcting signal used to correct the reading of the antimony pH sensor. The voltage produced by the antimony pH sensor will be an indication of the pH under measurement, and the current produced by the oxygen sensor may be employed to compensate or provide a correcting signal for the pH sensor voltage.

Ion exchange membranes are well known, and typical examples of these are polyacrylimide, polyamides, polyamines, polystyrene sulfonate butadiene copolymer.

By way of further example, the sensor described may, with suitable choice of chemicals, be used as a $CO_2$ sensor. Since $CO_2$ reacts with water to form carbonic acid, a measurement of the pH of a solution containing $CO_2$ will be a measure of the $CO_2$ concentration in the solution. The pH in fact varies as the logarithm of the partial pressure of the $CO_2$ in the solution. Accordingly, antimony may be used as an electrode as before, in place of the gold electrodes, with a silver-silver chloride reference electrode and an electrolyte typically consisting of sodium hydrogen carbonate and potassium chloride. In this event a gas permeable membrane would be used, to admit carbon dioxide to the electrodes.

Figure 21:
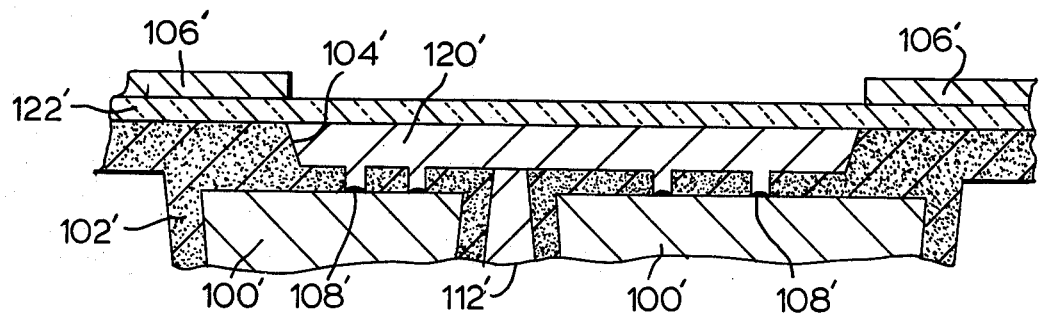
FIG. 21 is a cross-sectional view of a further embodiment of the invention.

When an ion specific sensor is made in accordance with the invention, one electrode will be located within the electrolyte, as before, but the other electrode may be located outside the electrolyte and membrane. This is shown in FIG. 21, where primed reference numerals indicate parts corresponding to those of FIG. 10. In the FIG. 21 embodiment, the electrodes 108' within the electrolyte may be silver, while the exterior electrode 106' may be silver-silver chloride. The electrode metallization 108 is deposited directly on the membrane 122', the latter being appropriately pretreated depending on the materials employed. The electrolyte 120' will contain the ion to be measured, and the membrane 122' will be a glass composition so that for a given concentration of the ion to be measured outside the glass layer, and dependent on the known ion concentration in the electrolyte, a voltage develops across the electrodes 106', 108' proportional to the ratio of the ion concentrations. Glass layer compositions for this purpose are well known. The electrode 108' within the electrolyte 120' may be a single large electrode or numerous small electrodes as previously described. The reference electrode 106' may be advantageously protected by a porous membrane (not shown) which acts as a filter to protect dirt in the solution being measured from depositing on the reference electrode 106'. Contacts 112', 114' to the reference electrode 106' and other electrodes 108' are made through the back of the device as previously described.

The thin film electrode assembly described is inexpensive and has a good performance relative to other polarographic electrode assemblies. The precise dimensional control which can be achieved enables the cathode geometry to be controlled and altered as required and thus, the electrode assembly performance can be precisely adjusted to meet sensor requirements.

Slow changes in temperature will cause corresponding changes in the output of the cell of about 2% per ° C, necessitating some temperature compensation circuit. This can be as simple as a matching thermistor connected to anode and cathode terminals.

Recalibration, which can be performed (e.g. for an $O_2$ sensor) by using the oxygen partial pressure in room air as the standard, requires only a few seconds since only the gain of the amplifier needs to be adjusted. With the thin film fabrication described, the residual current (at zero $PO_2$) remains essentially constant and very small so that a one-point calibration is sufficient. Thus, convenient and rapid measurements can be made on either bulk samples or in process streams. In fact, the close dimensional control of the thin film fabrication can obviate calibration of the devices entirely if membranes of known characteristics are applied in the final stage of device fabrication. If electrode geometry is reproducibly uniform amongst all devices of a wafer, it will suffice to calibrate a single sensor from that wafer or batch of wafers to characterize all others.

Although electrolytes and membranes as described will normally form part of cells and electrodes according to the invention, it will be realized that in some cases, the cell or electrode may be inserted directly into the solution under study, such solution then providing the electrolyte. In such cases, the cell need not be provided with its own electrolyte or membrane, although these items will normally serve to protect the cell and lengthen its life.

In addition to its use as a sensor, a cell of the kind described may also be used as a low level power source or battery.

The previous description has described electrochemical cells having two electrodes combined in one unit. In some circumstances, it is desirable to form single thin film electrode units, which units may be inserted into a test solution at different locations and which electrode units may then be electrically connected externally. For example, it may be desirable to insert single electrode units into a patient's blood stream at separated locations in order to read parameters of the blood or body fluids located between the electrodes. The methods of the invention may be used to form single thin electrode units similar to those previously described.

Figure 22:
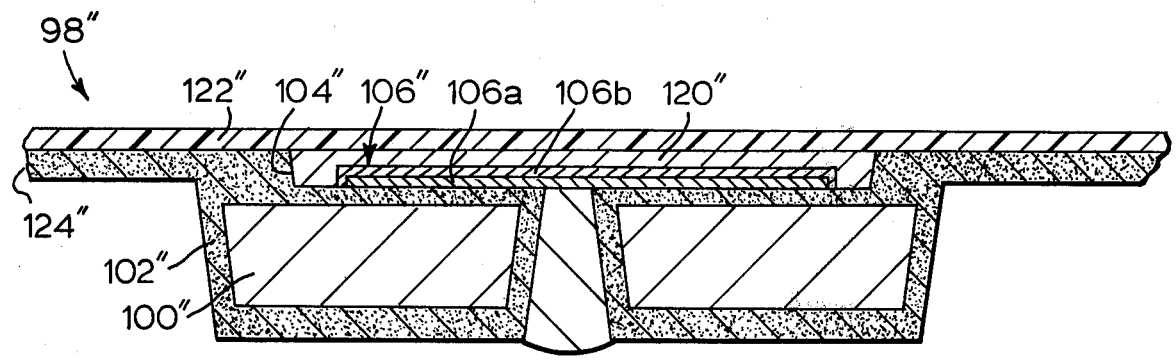
FIG. 22 to 27 are cross-sectional views each of a slightly different and further embodiment of the invention.

By way of example, reference is next made to FIG. 22, in which double primed reference numerals indicate parts corresponding to those of FIG. 10. The FIG. 22 electrode unit 98" is the same as the sensor 98 of FIG. 10, except that it contains only a single electrode 106" located in the well 104". Since the electrode unit 98" contains only a single electrode, only one of the contacts 112, 114 is required. In the drawing, contact 112" is shown, but it will be appreciated that either contact may be used.

The materials used in the FIG. 22 electrode unit will depend on the application required. For example, the electrode 106" may consist of a thin film layer of silver 106a, with a thin film coating of silver chloride 106b thereon. A thin film layer of platinum (not shown) may be deposited on the bottom surface of the well 104" prior to depositing the thin film layer of silver 106a; the platinum may under certain circumstances extend the usable life of the device. The electrolyte 120" may be dry buffered potassium chloride, and the porous membrane 122' may be a thin film polymer coating, as previously described.

Other materials may also be used for the FIG. 22 electrode unit. For example, the electrode unit 22 may be a calomel electrode unit, in which case the thin film layer 106a will be mercury (deposited on a layer of platinum, not shown), and the layer 106b will be mercurous chloride ($Hg_2Cl_2$). Other electrode, electrolyte and membrane materials may also be used, depending on the application.

Figure 23:
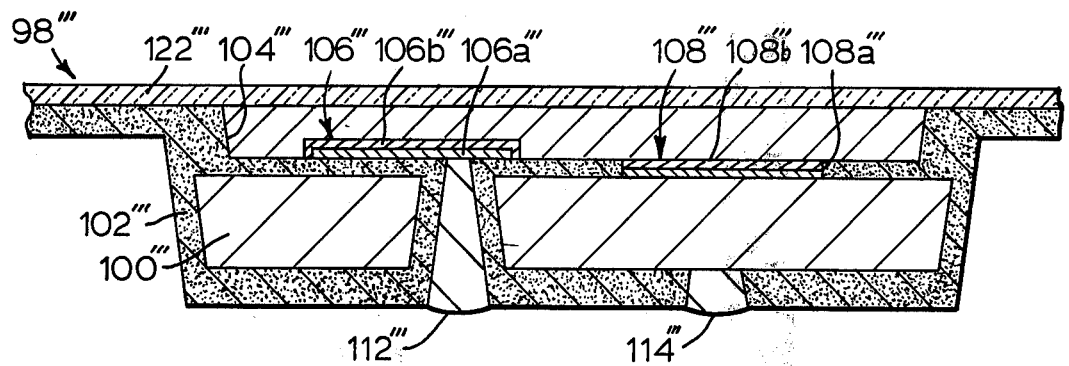

Reference is next made to FIG. 23, which shows a further embodiment of the thin film layer antimony pH cell shown in FIG. 21. In the FIG. 23 embodiment, in which triple primed reference numerals indicate parts corresponding to those of FIG. 21, both electrodes are located within the well 104''', i.e. within the electrolyte 120''' and beneath the membrane 122'''. As in the FIG. 21 embodiment, electrode 108''' may consist of a thin film layer of antimony (Sb) 108a''', with a thin film layer 108b of $Sb_2O_3$ formed thereon. The reference electrode 106''' may be a silver-silver chloride electrode as before, consisting of a thin film silver layer 106a''' with a thin film silver chloride layer 106b''' thereon. The electrolyte 120''' may be potassium chloride as before, and the membrane 122' may be an appropriate glass composition, as is well known. In the FIG. 23 embodiment, both electrodes 106''', 108''' are located in the well 104''', with contact 106''' being connected to the back via contact 112''' and electrode 108''' being connected to the back via contact 114'''. The electrodes 106'''', 108'''' are spaced apart in the well 104'''.

Thin film glass electrode cells may also be made according to the invention, as will now be described. By way of background, when a relatively thin glass membrane (which may range between 500 A and tens of micrometers in thickness) separates two electrolytes, a potential difference is observed across the glass. It is found that this glass electrode potential varies reproducibly with the activities of hydrogen and other ions in the electrolytes. Proper choice of glass composition provides a potential that varies as the log of the activity of a specific ion, and this may be essentially independent of the activities of other ions in the test solution.

When the indicator (i.e. the glass) electrode is an ion-responsive glass, two reference electrodes are normally used. An inner reference electrode (usually) immersed in a suitable standard electrolyte provides electrical contact to the inner surface of the glass electrode. The solution under test, which is in contact with the outer glass surface, is joined to an outer reference electrode by a suitable salt bridge (which can often be the test solution itself). Any potential changes between the two electrodes reflect changes in the glass (indicator) electrode potential, which can then be related to alterations in ion activity within the test solution. A suitable inner reference electrode is generally either the calomel, or silver-silver chloride in a buffered chloride electrolyte solution. Dry connections to the glass membrane by means of a silver film have been used and eliminate the need for the electrolyte solution.

Figure 24:
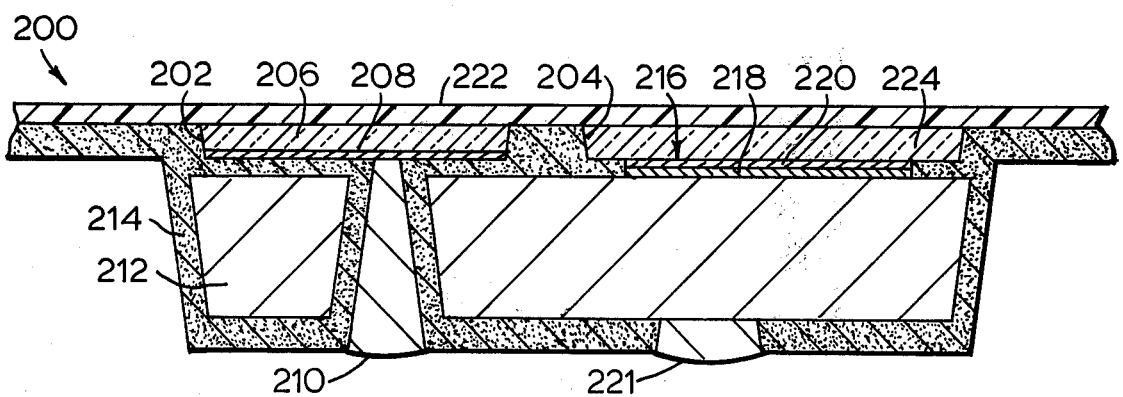

A glass electrode cell according to the invention is shown in FIG. 24. The FIG. 24 cell is essentially the same in structure as the cells of FIG. 10 and following, and is formed in the same way, and only the differences will be described.

Firstly, it will be seen that the cell of FIG. 24, which cell is indicated generally at 200, contains two wells 202, 204. The well 202 contains an inner electrode of pH sensitive glass 206 sputtered or vacuum deposited on a silver film 208 to form a dry contact reference electrode. The silver film 208 coats the bottom surface of the well 202. Contact is made to the film 208 via back contact 210, which extends through the silicon substrate 212 and is insulated from the silicon by a layer of silicon dioxide 214 as before. pH sensitive glasses are well known, and are discussed for example in the recently published text "Transducers for Bio-Medical Measurements: Principles and Applications" by Richard S. C. Cobbold, John Wiley and Sons, Inc., published in 1974.

The well 204 contains a reference electrode 216, which may consist of a thin film silver layer 218 and a thin film silver chloride 220, or alternatively it may be a calomel electrode. External connection to electrode 216 is made via the substrate 212 and back contact 221. The porous membrane 222 may be a thin film polymer as before, and the electrolyte 224 may be any suitable material, depending on the materials used for the electrode 216.

Figure 25:
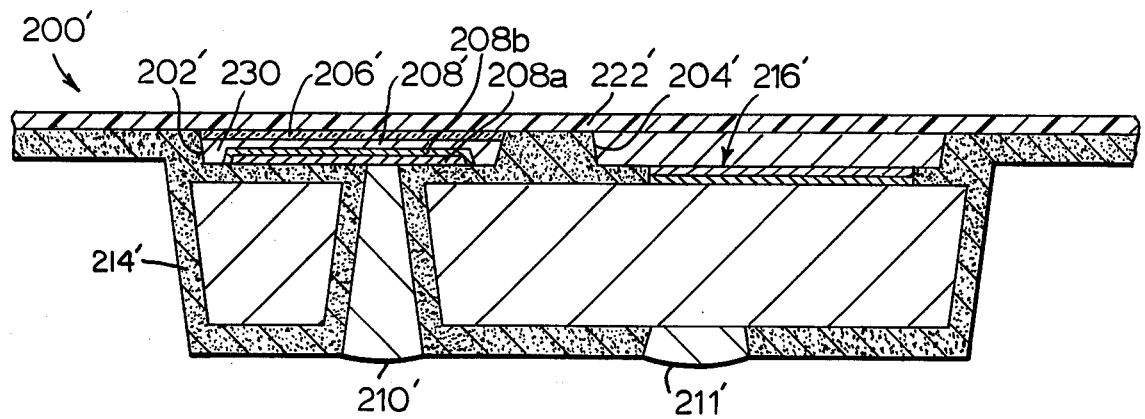

Reference is next made to FIG. 25, which shows a pH sensor which is the same as that of FIG. 24, except for minor changes. In FIG. 25, primed reference numerals indicate parts corresponding to those of FIG. 24.

The difference between the FIG. 25 and FIG. 24 embodiments is that in the FIG. 25 version, the electrode 208' is a silver-silver chloride electrode, consisting of a silver thin film layer 208a, coated with a thin film silver chloride layer 208b. Alternatively, the electrode 208' may be a calomel electrode. The electrode 208' is located in an appropriate electrolyte 230, with the pH sensitive glass 206' located immediately above the electrolyte and beneath the porous membrane 222'. The remaining electrode 216 is, as before, silver-silver chloride or calomel, depending on the nature of the electrode 202'. In the FIG. 25 embodiment, the inner and outer reference electrodes 208', 216' may be formed in the same step.

The thin film electrodes of the invention may also be used for anion and cation measurements. Through a proper selection of the glass composition, it is possible to change the relative sensitivity of the electrode to various cation types. However, with the single exception of the positive hydrogen ion, it is not possible to achieve a composition that is sensitive to just one cation type and which is insensitive to all others that may be present in the test solution. The Nernst equation for an ideal two-ion electrolyte illustrates a measure of the sensitivity of the glass:

$$E = E_o + \frac{RT}{F} \ln (a_i + K_{ij}a_j),$$

where $a_i$, $a_j$ are the respective activities of the two ion species and $K_{ij}$ is the selectivity or the relative sensitivity of the electrode to ion $j$ as compared to ion $i$.

The relative values of $K_{ij}$ for differing ion types have been experimentally determined for a number of glass compositions. The sodium glass NAS 11-18 is 200 times more sensitive to sodium than to potassium for test solutions of the same pH. For the potassium selective glass NAS 27-4 the selectivity for potassium ions is 10 times that for sodium ions. Compensation for interfering ion species can readily be achieved in thin film structures by forming several electrodes with different ion selectivities on the same substrates. The potentials from each sensor reflect, in a well defined manner, the influences of each ion species on the electrodes and can be used in simple signal processing to extract each ion activity.

Figure 26:
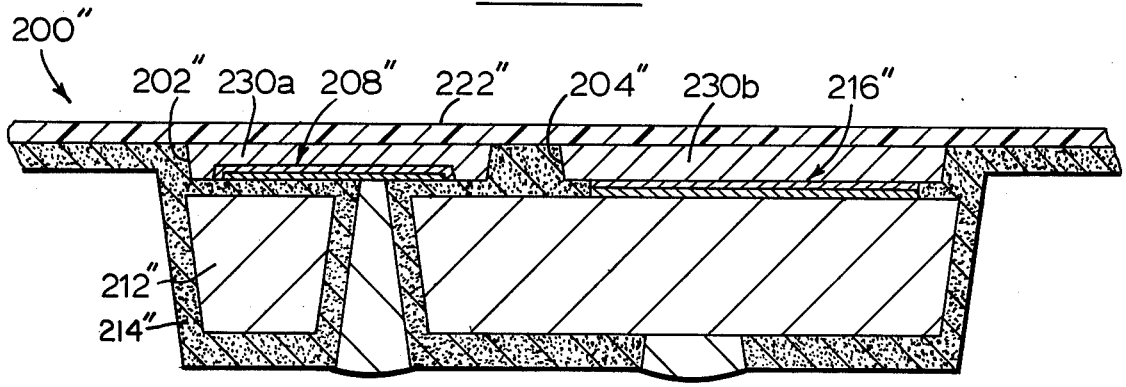

Certain solid state and liquid substances exhibit a selective Nernstian response to ions of a particular type. Recently, through an improved understanding of the mechanism of ion transport and through the discovery of new materials that exhibit improved selectivity, a wide range of ion selective electrodes has become commercially available. A liquid ion exchanger consists of a solution of a certain high molecular weight substance in a water insoluble organic solvent. An example of a thin film liquid membrane electrode permeable to to $Ca++$ is shown in FIG. 26. The FIG. 26 structure is the same as that of FIG. 25, except for the omission of the pH sensitive glass, and double primed reference numerals indicate parts corresponding to those of FIGS. 24 and 25.

In the FIG. 26 structure, the electrodes 208", 216" are the same as those of FIG. 25, but the pH sensitive glass 206' has been omitted. The materials contained in the wells 202", 204" are different. The well 202" contains an organic exchange medium, which may be deposited through a metal mask as previously described. The organic exchange medium, indicated at 230a, may typically be 0.1M $CaCl_2$ and 0.1M calcium salt of didecyl phosphoric acid in dioctylphenyl-phosphonate together with a buffered chloride electrolyte. The porous membrane filter 222" acts as a container for the organic exchange medium 230a and the calcium chloride is an internal reference solution for $Ca++$. The electrolyte 230b in well 204 is typically simply a buffered chloride solution.

Various kinds of membranes may be used according to the invention, depending on the application of the invention. For example, solid state membranes based on single crystals of rare earth fluorides, polycrystalline silver sulfide, fused mixtures of silver sulfide and halides, metal sulfides in a matrix of silver sulfide, and a variety of solid organic materials all exhibit selective electrode properties. All these materials can be formed as thin film layers between or as porous filter membranes and appropriate thin film reference electrodes to yield cation and anion selective sensors.

Figure 27:
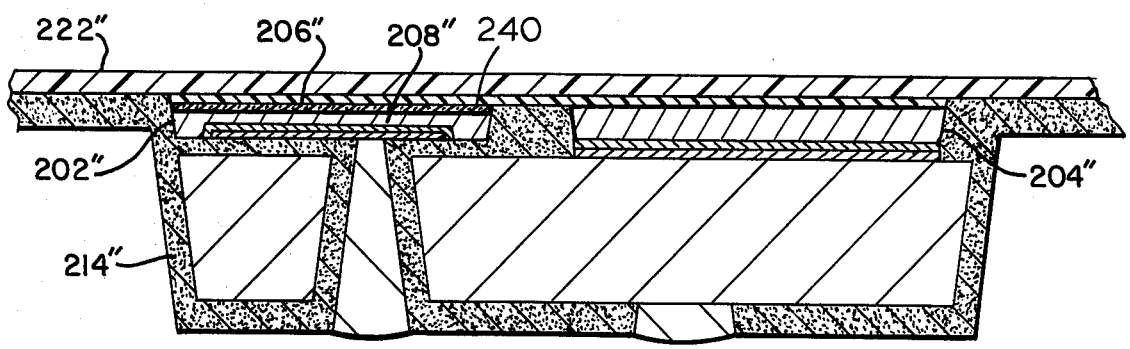

Reference is next made to FIG. 27, which shows a thin film $CO_2$ cell, with appropriate selection of materials. The basic principle of a $CO_2$ cell is to allow the unknown $CO_2$ source to equilibrate with an aqueous solution of sodium hydrogen carbonate and to measure the pH change arising from the reaction $CO_2$ with water to yield carbonic acid. The FIG. 27 cell is almost the same as the FIG. 25 cell, and double primed reference numerals in FIG. 27 indicate corresponding parts. The difference between the cells is that the FIG. 27 cell has a porous filter membrane 240 located beneath membrane 222″. Membrane 222″ is now simply a gas permeable membrane, e.g. Teflon (TM). The filter membrane 240 extends across both wells 202″, 204″, and the partition between the wells and provides for electrochemical contact between the pH sensitive glass 206″ and the electrode 216″. The electrode 208″ will usually be silver-silver chloride, while reference electrode 216″ may be silver-silver chloride or calomel. The electrolyte in well 202″ will usually be a buffered chloride electrolyte, while the electrolyte in well 204″ may be 0.1N potassium chloride and 0.11N sodium hydrogen carbonate.

Various further applications of the invention are possible, for example, as enzyme sensors: In this mode, an immobilized enzyme is placed on the porous filter membrane so that the enzyme will contact the test solution. The device may then be used as a gas or other ion sensor with the immobilized enzyme, in a differential mode, to indicate the presence and quantity of the enzyme in the test solution.

In all cases, the electrodes of the electro-chemical cells or electrode units according to the invention can be the base inputs of field effect transistors or integrated circuits formed on the same substrate, in order to reduce signal loss and interference in processing the signals from the electrodes.

The term "thin film" as used in this description and in the appended claims, means a film of not more than 25 micrometers thickness. Preferably the films when deposited will (except for the membranes) be 20,000 Å thickness or less. Plating may be used to increase the thickness if desired. Catalytic and other known depositions may be used.

What I claim is:
1. An electro-chemical cell comprising:
   a. a conducting substrate having a first face having a first thin film insulating layer thereon,
   b. said first insulating layer having a plurality of small holes therein, and a plurality of thin film microcathodes located in said holes, said microcathodes being electrically connected to said substrate,
   c. a continuous thin film anode layer on said first insulating layer and surrounding said microcathodes, said anode layer being electrically insulated from said microcathodes and said substrate by said first insulating layer,
   d. a cathode contact connected electrically to said substrate and thereby being electrically connected to said cathodes,
   e. an anode contact electrically connected to said anode layer,
   f. a layer of electrolyte located over said microcathodes and said anode layer and connecting the same,
   g. and a membrane of selected permeability covering said electrolyte.

2. An electro-chemical cell according to claim 1 wherein said substrate includes a second face opposite said first face and having a second insulating layer thereon, said second insulating layer having a cathode contact hole therein, said cathode being located in said cathode contact hole.

3. An electro-chemical cell according to claim 2 wherein said second insulating layer, said substrate, and said first insulating layer include aligned holes therein extending through to said anode layer, said anode contact being located in said aligned holes, said hole in said conductive substrate having a wall of a thin film insulating material which insulates said anode contact against contact with said conductive substrate.

4. An electro-chemical cell according to claim 3 wherein said conductive substrate is doped silicon, and said first and second insulating layers and said wall are all silicon dioxide.

5. An electro-chemical cell according to claim 1 wherein said microcathodes are of gold, and said anode layer is of silver, said cell further including a layer of silver chloride on said anode layer, said membrane being a gas permeable membrane.

6. An electro-chemical cell according to claim 1 wherein said membrane is a polymer membrane formed by depositing a selected material over said electrolyte and then polymerizing such material.

7. An electro-chemical cell having a conductive substrate having first and second opposed faces, a first thin film insulating layer on said first face and a second thin film insulating layer on said second face, first and second electrodes arranged over said first face, said first electrode being electrically connected to said substrate and said second electrode being insulated from said substrate and said first electrode by said first insulating layer, said second insulating layer having a hole therein, a contact in second hole and electrically connected to said substrate thereby forming an electrical connection to said first electrode, said second insulating layer, said substrate and said first insulating layer having aligned holes therein, a further contact in said aligned holes and extending to said second electrode, the hole in said substrate having a wall of a thin film insulating material to insulate said further contact from said substrate.

8. An electro-chemical cell according to claim 1 wherein said first insulating layer includes a well therein, at least said first electrode being located in said well.

9. An electro-chemical cell according to claim 8 wherein said first electrode comprises a plurality of thin film microcathodes located in small holes in said first insulating layer, said second electrode comprises a continuous thin film anode on said first insulating layer in said well and surrounding said microcathodes but insulated therefrom by said first insulating layer, a layer of electrolyte filling said well to a level flush with its top, and a thin film membrane of selected permeability covering said well and said first insulating layer surrounding said well.

10. A thin film electrode structure comprising a conductive substrate having a first face and a second face opposed to said first face, a first thin film insulating layer on said first face and having a well therein, a second thin film insulating layer on said second face, a thin film electrode in said well and electrically connected to said substrate, said second insulating layer having a hole therein, and a contact located in said hole and being in electrical contact with said substrate, said contact thereby being electrically connected to said electrode.

11. The invention according to claim 10 including an electrolyte filling said well, and a membrane of selected permeability covering said well and the insulating layer surrounding said well.

12. A thin film electrode structure comprising a conductive substrate having a first face and a second face opposed to said first face, a first thin film insulating layer on said first face, a second thin film insulating layer on said second face, an electrode over said first face and insulated from said substrate by said first insulating layer, said first and second insulating layers and said substrate including aligned holes therein, a contact located in said aligned holes and extending from said second insulating layer through to said electrode and being connected thereto, said substrate having a thin film insulating layer defining the wall of the hole therein and insulating said contact from said substrate.

* * * * *